US012661420B2

(12) United States Patent
Taylor et al.

(10) Patent No.: US 12,661,420 B2
(45) Date of Patent: Jun. 23, 2026

(54) SELF-STERILISING URINARY CATHETER

(71) Applicant: CLEAN BLUE LIMITED, Headley (GB)

(72) Inventors: Daniel Christopher Taylor, Headley (GB); Cara Louise Taylor Cooper, Ickleton (GB); Charles Matthew Dean, Ickleton (GB); Peter Ian Money, Ickleton (GB)

(73) Assignee: CLEAN BLUE LIMITED, Headley (GB)

( * ) Notice: Subject to any disclaimer, the term of this patent is extended or adjusted under 35 U.S.C. 154(b) by 699 days.

(21) Appl. No.: 17/915,942

(22) PCT Filed: Mar. 30, 2021

(86) PCT No.: PCT/GB2021/050784
§ 371 (c)(1),
(2) Date: Sep. 29, 2022

(87) PCT Pub. No.: WO2021/198672
PCT Pub. Date: Oct. 7, 2021

(65) Prior Publication Data
US 2023/0218790 A1      Jul. 13, 2023

(30) Foreign Application Priority Data

Mar. 30, 2020     (GB) ...................................... 2004616

(51) Int. Cl.
*A61L 2/10*          (2026.01)
*A61L 2/26*          (2006.01)
(Continued)

(52) U.S. Cl.
CPC .................................... *A61L 2/10* (2013.01); *A61L 2/26* (2013.01); *A61M 25/0017* (2013.01); *A61L 2103/15* (2026.01); *A61L 2202/11* (2013.01)

(58) Field of Classification Search
CPC .......... A61L 2/10; A61L 2/26; A61L 2202/11; A61L 2202/24; A61L 2/084; A61L 2/08;
(Continued)

(56) References Cited

U.S. PATENT DOCUMENTS 5,260,020 A * 11/1993 Wilk ................. A61M 25/0017
                                                    606/29
7,396,354 B2 * 7/2008 Rychnovsky .......... A61N 5/062
                                                    606/7
(Continued)

FOREIGN PATENT DOCUMENTS

CN          102811767 A      12/2012
CN          102811767 B       5/2016
(Continued)

OTHER PUBLICATIONS

Wolkenstorfer, Heltschl, Heltschl, Device for Medical Radiation, 2009, Machine Translation (Year: 2009).*
(Continued)

*Primary Examiner* — Rebecca E Eisenberg
*Assistant Examiner* — Brandon W. Levy
(74) *Attorney, Agent, or Firm* — MARSHALL, GERSTEIN & BORUN LLP

(57) ABSTRACT

The present invention relates to urinary catheters, in particular indwelling urinary catheters, with self-sterilising capabilities. There is disclosed a catheter for insertion into the bladder of a patient, the catheter comprising an elongate body having a distal portion configured to reside in the patient's body, and a proximal portion configured to be left outside of the body of the patient. The catheter may further comprise at least one light generator provided within the distal portion of the elongate body so as to emit light, wherein said light comprises sterilising light.

18 Claims, 7 Drawing Sheets

(51) Int. Cl.
*A61M 25/00* (2006.01)
*A61L 103/15* (2026.01)

(58) Field of Classification Search
CPC .............. A61L 2202/14; A61L 2/0047; A61M
25/0017; A61M 2025/0019; A61M
2205/051; A61B 1/121; A61B 1/015;
A61B 5/0086; A61B 18/24; A61B
1/0684; A61N 5/0601; A61N 5/0624;
A61N 2005/0652; A61N 2005/061; A61N
2005/063; A61N 2005/0662; A61N
2005/0661; A61N 5/067; A61N
2005/0663
See application file for complete search history.

(56) References Cited

U.S. PATENT DOCUMENTS

| | | | |
|---|---|---|---|
| 8,574,490 | B2 | 11/2013 | Haytman et al. |
| 9,550,005 | B2 | 1/2017 | Lin et al. |
| 2001/0003800 | A1 | 6/2001 | Crowley |
| 2004/0092890 | A1 | 5/2004 | Ash |
| 2010/0016844 | A1* | 1/2010 | Patel, Jr. ................ A61B 90/30 606/15 |
| 2010/0198139 | A1* | 8/2010 | Glickman ......... A61M 25/0017 604/30 |
| 2012/0310310 | A1 | 12/2012 | Paterok |
| 2013/0267888 | A1* | 10/2013 | Rhodes ............. A61M 25/0017 604/21 |
| 2014/0107496 | A1 | 4/2014 | Hellstrom et al. |
| 2014/0235942 | A1* | 8/2014 | Hellstrom ............ A61B 1/0615 128/200.26 |
| 2015/0126976 | A1* | 5/2015 | Tang ................. A61M 25/0012 604/328 |
| 2015/0190649 | A1 | 7/2015 | Gelfand et al. |
| 2015/0283277 | A1 | 10/2015 | Schafer et al. |
| 2016/0213945 | A1 | 7/2016 | Burwell et al. |
| 2017/0014538 | A1 | 1/2017 | Rantala |
| 2017/0100494 | A1* | 4/2017 | Dobrinsky .............. A61L 2/088 |
| 2019/0168023 | A1 | 6/2019 | Eltorai |

FOREIGN PATENT DOCUMENTS

| | | | | |
|---|---|---|---|---|
| DE | 60112434 | T2 | 3/2006 | |
| DE | 102010006035 | A1 | 7/2011 | |
| DE | 112011100343 | A5 | 12/2012 | |
| EP | 1284780 | B1 | 5/2008 | |
| EP | 2111896 | A1 * | 10/2009 | ........... A61N 5/0603 |
| EP | 2528658 | B1 | 2/2015 | |
| EP | 2866892 | A1 | 5/2015 | |
| JP | 3553595 | B2 | 8/2004 | |
| WO | WO-2001085249 | A1 | 11/2001 | |
| WO | WO-2008/024478 | A2 | 2/2008 | |
| WO | WO-2011091787 | A1 | 8/2011 | |
| WO | WO-2012/170401 | A2 | 12/2012 | |
| WO | WO-2013049491 | A1 | 4/2013 | |
| WO | WO-2014004762 | A1 | 1/2014 | |
| WO | WO-2015153172 | A1 | 10/2015 | |
| WO | WO-2015168129 | A1 | 11/2015 | |

OTHER PUBLICATIONS

"Blood flow monitor could save lives in heart surgery", Flinders University, downloaded from the Internet at: <https://news.flinders.edu.au/blog/2019/07/10/blood-flow-monitor-could-save-lives/> posted Jul. 10, 2019.

"Why Oralucent is "light years" ahead", Oralucent, downloaded from the Internet at: <https://oralucent.com/pages/light-technology> publicly available 2020.

Bak et al., A prototype catheter designed for ultraviolet C disinfection, J. Hosp. Infect., 84(2):173-7 (Jun. 2013). doi: 10.1016/j.jhin.2013.03.003. Epub May 10, 2013.

Bak et al., Dose requirements for UVC disinfection of catheter biofilms, 25(4):289-96 (2009). doi: 10.1080/08927010802716623.

Bak et al., Potential in vivo UVC disinfection of catheter lumens: estimation of the doses received by the blood flow outside the catheter tip hole, Photochem. Photobiol., 87(2):350-6 (Mar.-Apr. 2011). doi: 10.1111/j.1751-1097.2011.00887.x. Epub Jan. 31, 2011.

Dai et al., Ultraviolet-C irradiation for prevention of central venous catheter-related infections: an in vitro study, Photochem. Photobiol., 87(1):250-5 (Jan.-Feb. 2011). doi: 10.1111/j.1751-1097.2010.00819.x. Epub Nov. 12, 2010.

Enwemeka et al., Blue 470-nm light kills methicillin-resistant *Staphylococcus aureus* (MRSA) in vitro, Photomed. Laser Surg., 27(2):221-6 (Apr. 2009).

Espada Acne Clearing Blue Light Pen, Foreo, downloaded from the Internet at: https://www.ulta.com/p/espada-acne-clearing-blue-light-pen-xlsImpprod18671029, publicly available Aug. 18, 2021.

Fontana et al., The effect of blue light on periodontal biofilm growth in vitro, Lasers Med. Sci., 30(8):2077-86 (Nov. 2015).

Giannelli et al., Effects of photodynamic laser and violet-blue led irradiation on *Staphylococcus aureus* biofilm and *Escherichia coli* lipopolysaccharide attached to moderately rough titanium surface: in vitro study, Lasers Med. Sci., 32(4):857-64 (May 2017).

Gomez et al., Photo Inactivation of *Streptococcus* mutans Biofilm by Violet-Blue light, Curr. Microbiol., 73(3):426-33 (Sep. 2016).

Halstead et al., Antibacterial Activity of Blue Light against Noso-comial Wound Pathogens Growing Planktonically and as Mature Biofilms, Appl. Environ. Microbiol., 82(13):4006-16 (Jun. 2016).

International Application No. PCT/GB2021/050784, International Search Report, mailed Jul. 12, 2021.

International Application No. PCT/GB2021/050784, Written Opinion, mailed Jul. 12, 2021.

Kingery, Catheter Innovation Destroys Dangerous Biofilms, Duke Pratt School of Engineering, downloaded from the Internet at: <https://pratt.duke.edu/about/news/catheter-innovation-destroys-dangerous-biofilms#:~:text=Duke%20University%20engineers%20have%20developed,infectious%20film%20from%20its%20moorings> dated Mar. 25, 2014.

Lubart et al., A possible mechanism for the bactericidal effect of visible light, Laser Ther., 20(1):17-22 (2011).

MacLean et al., Inactivation of Bacterial Pathogens following Exposure to Light from a 405-Nanometer Light-Emitting Diode Array, Appl. Environ. Microbiol., 75(7):1932-7 (Apr. 2009).

Mau, Can an at-home LED light therapy mask cure acne? We tried it, Fashionista, downloaded from the Internet at: <https://fashionista.com/2014/07/illumask-light-therapy> (published Jul. 24, 2014).

McKenzie et al., Photoinactivation of bacteria attached to glass and acrylic surfaces by 405 nm light: potential application for biofilm decontamination, Photochem. Photobiol., 89(4):927-35 (Jul.-Aug. 2013).

Pereira Rosa et al., In vitro effectiveness of 455-nm blue LED to reduce the load of *Staphylococcus aureus* and Candida albicans biofilms in compact bone tissue, Lasers Med. Sci., 31(1):27-32 (Jan. 2016).

Roche et al., A light-reflecting balloon catheter for atraumatic tissue defect repair, Sci. Transl. Med., 7(306):306ra149 (Sep. 2015). doi: 10.1126/scitranslmed.aaa2406. Epub Sep. 23, 2015.

TRIA Skin Perfecting Blue Light, downloaded from the Internet at: <https://www.lovelyskin.com/o/tria-skin-perfecting-blue-light>, publicly available Sep. 24, 2013.

Vollmerhausen et al., Visible and UVA light as a potential means of preventing *Escherichia coli* biofilm formation in urine and on materials used in urethral catheters, J. Photochem. Photobiol. B, 170:295-303 (May 2017).

Wang et al., Antimicrobial Blue Light Inactivation of Gram-Negative Pathogens in Biofilms: In Vitro and In Vivo Studies, J. Infect. Dis., 213(9):1380-7 (May 2016).

Wang et al., Antimicrobial blue light inactivation of pathogenic microbes: state of the art, Drug Resist Updt., 33-35:1-22 (Nov. 2017).

* cited by examiner

SELF-STERILISING URINARY CATHETER

CROSS-REFERENCE TO RELATED APPLICATIONS

This is the United States National Phase of International Patent Application No. PCT/GB2021/050784, filed Mar. 30, 2021, which claims priority to GB 2004616.5, filed Mar. 30, 2020.

TECHNICAL FIELD

The present invention relates to urinary catheters, in particular indwelling urinary catheters.

BACKGROUND

Catheters are commonly used to deliver or remove fluids from a patient. In essence, a catheter typically comprises an elongated body defining a lumen for passing a fluid into or out of the patient's body. In the field of catheters, the term "lumen" refers to a fluid pathway defined within the catheter that fluidly connects a space inside the patient's body to outside of the body.

Catheters are commonly used in urology. A urinary catheter is typically inserted into the patient's bladder. A lumen runs along the length of the catheter. On one end, the lumen fluidly communicates with the internal volume of the bladder through an opening provided on a portion of the catheter which is inserted into the bladder. On the other end, the lumen extends to an opening outside the patient's body. Therefore, using the lumen, fluid in the bladder may be drained through the lumen out of the patient. The drained fluid may be collected outside the patient's body, such as into a urine bag, which may be worn by the patient. A lumen in the urinary catheter may be used instead for delivering fluid into the bladder, such as a saline solution for flushing out the bladder.

Urinary catheters are inserted into the bladder in one of two ways. The first way, in the case of indwelling or intermittent catheters, is to insert the catheter through the urethra and into the bladder. The second way, in the case of supra-pubic catheters, is to open a hole through the skin and the bladder wall and insert the catheter through the hole into the bladder.

Urinary catheters, notably intermittent catheters, may be inserted into the patient's bladder for a short amount of time, such as for one-off drainage. In other cases, urinary catheters may be inserted into the patient's bladder on a long-term basis. For example, supra-pubic catheters are commonly left in place for several weeks at a time. Indwelling catheters are commonly left in place for several months at a time.

Urinary catheters are known to cause catheter associated urinary tract infections (CAUTIs). The inventor has found that infections are typically caused by pathogens, especially bacteria, viruses, prions and fungi, growing on a surface of the urinary catheter. The inventor has found that pathogens can adhere to the surface of the urinary catheter and multiply, developing a layer of material called "biofilm" on the surface of the urinary catheter. The biofilm facilitates further growth of pathogens, and is difficult to remove. The biofilm may also facilitate the development of antibiotic resistance. In the most severe cases, CAUTIs can lead to mortality. In moderate cases, CAUTIs can cause discomfort and pain to the patient.

In the United Kingdom, of all patients with a long-term catheter, 24% develop an infection that requires treatment at an average cost of £645. Typically, medications such as antibiotics and pain relief medications may be prescribed to treat or reduce the likelihood of developing CAUTIs, or at least lessen the symptoms of such infections. However, bacteria with antibiotic resistance are a growing problem, and antibiotics could eventually become entirely ineffective at preventing or treating these infections in the not too distant future.

Therefore, in order to reduce the likelihood of CAUTIs in the first place, urinary catheters typically require frequent changes, which changes are inconvenient and unpleasant to the patient. Furthermore, the changing of a catheter typically requires the expertise of healthcare professionals, thereby adding to the cost of the use of urinary catheters on an ongoing basis. In addition, frequent catheter changes due to infection may pose a financial and environmental cost in terms of the materials that are discarded and the travel incurred.

US 2013/0267888 A1 discloses a urinary catheter with a fibre optic within the catheter. The fibre optic serves to conduct light axially along the catheter. An external light source is provided to introduce light into the fibre optic. The radiation is a non-ultraviolet light, particularly having a wavelength between 380 nm and 900 nm at a high intensity sufficient to inactivate certain pathogens without harming the patient. The light therefore reflects within the fibre optic along the length of the catheter and is distributed along catheter, thereby inactivating pathogens adhered to the catheter. As an alternative, a lumen internally coated with a reflective coating can be provided in place of the fibre optic.

As found by the present inventor, irradiating the entire catheter at a sufficient intensity to inactive pathogens requires a relatively large amount of power. This means that either the external light source must be attached to a mains power supply, or a sufficiently large battery must be provided. If a mains power supply is to be used, electrical safety concerns and regulatory burden may arise. As found by the inventor, on one hand, large batteries are heavy and cumbersome to carry around by the patient and, on the other hand, small batteries require frequent charging/replacing in order to provide sufficient electrical power to power the external light source. As can be seen, this is inconvenient and places certain limitations on the mobility of the patient.

As found by the present inventor, another factor that contributes to the high power consumption of the external light source is that the use of an optical fibre results in poor optical efficiency. For example, an arrangement using a fibre optic has an overall optical efficiency of around 10%. The optical efficiency could be somewhat improved by using a fibre optic with a numerical aperture that matches the light source, and by controlling the air gap between the external light source and the fibre optic. In the best case, the optical efficiency can reach about 16%, which is still a poor efficiency.

There is thus room for improvement in terms of energy efficiency whilst maintaining effective sterilisation of urinary catheters. Improved energy efficiency will in turn allow a more portable device that can be used for longer periods without requiring intervention such as recharging or changing batteries.

SUMMARY

There is disclosed a catheter for insertion into the bladder of a patient, the catheter comprising an elongate body having a distal portion configured to reside in the patient's body, and a proximal portion configured to be left outside of the body of the patient. The catheter may further comprise at least one light generator provided within the distal portion of the elongate body so as to emit light, wherein said light comprises sterilising light.

The light may be blue or violet.

The light may comprise radiation within a spectral range of 390 to 500 nm.

The total power of the radiation within the spectral range of 390 to 500 nm may be at least 80% of the total power of the light.

The light may consist of radiation within a spectral range of 390 to 500 nm.

The elongate body may define an internal lumen in fluid communication with the exterior of the elongate body through a fluid port. The fluid port may be located in an end section of the distal portion, the end section being configured to reside within the bladder.

The at least one light generator may comprise a distal light generator positioned to irradiate the fluid port.

The distal light generator and the fluid port may be co-disposed at the same longitudinal position along the elongate body.

The fluid port may comprise two openings. The two openings may be co-disposed at the same longitudinal position along the elongate body.

The distal light generator may be substantially equidistant from both openings of the fluid port.

The catheter may comprise a securing member that is configured to prevent the distal portion from exiting the patient's body.

The securing member may be configured to reside within the patient's bladder

The securing member may be an inflatable member. The inflatable member may be configured, when inflated, to prevent the distal portion from exiting the patient's body. The elongate body may define an inflation lumen in fluid communication with the inflatable member.

The at least one light generator may comprise a proximal light generator positioned to irradiate and sterilise an area of a portion of the elongate body on the proximal side of the securing member.

Said area may comprise the exterior surface of said portion of the elongate body.

Said area may comprise the internal surface of the internal lumen within said portion of the elongate body.

The proximal light generator may be positioned such that the portion of the elongate body whose area is irradiated and sterilised by the proximal light generator is, when the distal portion is in the patient's body including the bladder, located between the securing member and the internal urethral sphincter.

The proximal light generator may be positioned such that the portion of the elongate body whose area is irradiated and sterilised by the proximal light generator is, when the distal portion is in the patient's body including the bladder, located on the proximal side of the internal urethral sphincter.

The proximal light generator may be configured to irradiate and sterilise a complete cylindrical section of the area of the elongate body.

The intensity of the sterilising light measured at the area of the elongate body may be at least 0.05 mW/mm², optionally at least 0.08 mW/mm², throughout the cylindrical section.

The cylindrical section may be at least about 3 mm long in the longitudinal direction of the elongate body.

The proximal light generator may comprise first and second light generating elements.

The first light generating element may face the central axis of the elongate body. The second light generating element may face an opposite direction to the first light generating element.

The first light generating element may be configured to generate a greater power of sterilising light than the second light generating element, optionally twice as much power of sterilising light as the second light generating element.

The elongate body may define an elongate lighting cavity. The at least one light generator may be provided within the elongate lighting cavity.

The elongate lighting cavity may restrict the translation and/or rotation of the at least one light generator relative to the elongate body.

The elongate lighting cavity may have a non-circular transverse cross-section.

The at least one light generator may be provided on a flexible printed circuit board.

The elongate lighting cavity may be dimensioned to maintain a compressive force on the flexible printed circuit board.

The elongate lighting cavity may be part of a lighting lumen extending between the proximal portion and the distal portion of the elongate body.

The catheter may comprise electrical wiring disposed in the lighting lumen. The electrical wiring may be configured to supply electrical power to the at least one light generator.

The flexible printed circuit board may extend through the lighting lumen into the proximal portion of the elongate body.

The catheter may further comprise an power connection at the proximal portion for supplying electrical power to the at least one light generator.

The power connection may be configured to be disconnectable by a force smaller than the force required to pull the catheter out of the bladder.

The catheter may further comprise a red-infrared light generator configured to emit red and/or infrared light and positioned to irradiate an area of a portion of the elongate body.

The red-infrared light generator may be configured to emit red light within a spectral range of 620 to 700 nm and/or infrared light within a spectral range of 800 to 2500 nm. The light emitted by the red-infrared light generator may consist of radiation within a spectral range 620 to 2500 nm, or 620 to 700 nm, or 800 to 2500 nm.

There is also disclosed a method of producing a catheter. The method may comprise providing a catheter comprising an elongate body having a distal portion and a proximal portion. The elongate body may define first and second internal lumens in fluid communication with the exterior of the elongate body respectively through first and second fluid ports, the first and second fluid ports being located in said distal portion. The method may comprise providing at least one light generator. The method may comprise inserting the at least one light generator into the distal portion of the second internal lumen.

The method may comprise the step of sealing the second fluid port to close it.

The step of sealing the second fluid port may comprise injecting a sealant into the second fluid port to close the second fluid port, and optionally to fix the at least one light generator in place.

The distal portion may be configured to reside in the patient's body. The catheter may further comprise a securing member that is configured to prevent the distal portion from exiting the patient's body.

The securing member may be configured to reside within the patient's bladder.

The securing member may be an inflatable member. The inflatable member, when inflated, may be configured to prevent the distal portion from exiting the patient's body.

FIGURES

DETAILED DESCRIPTION

Figure 1:
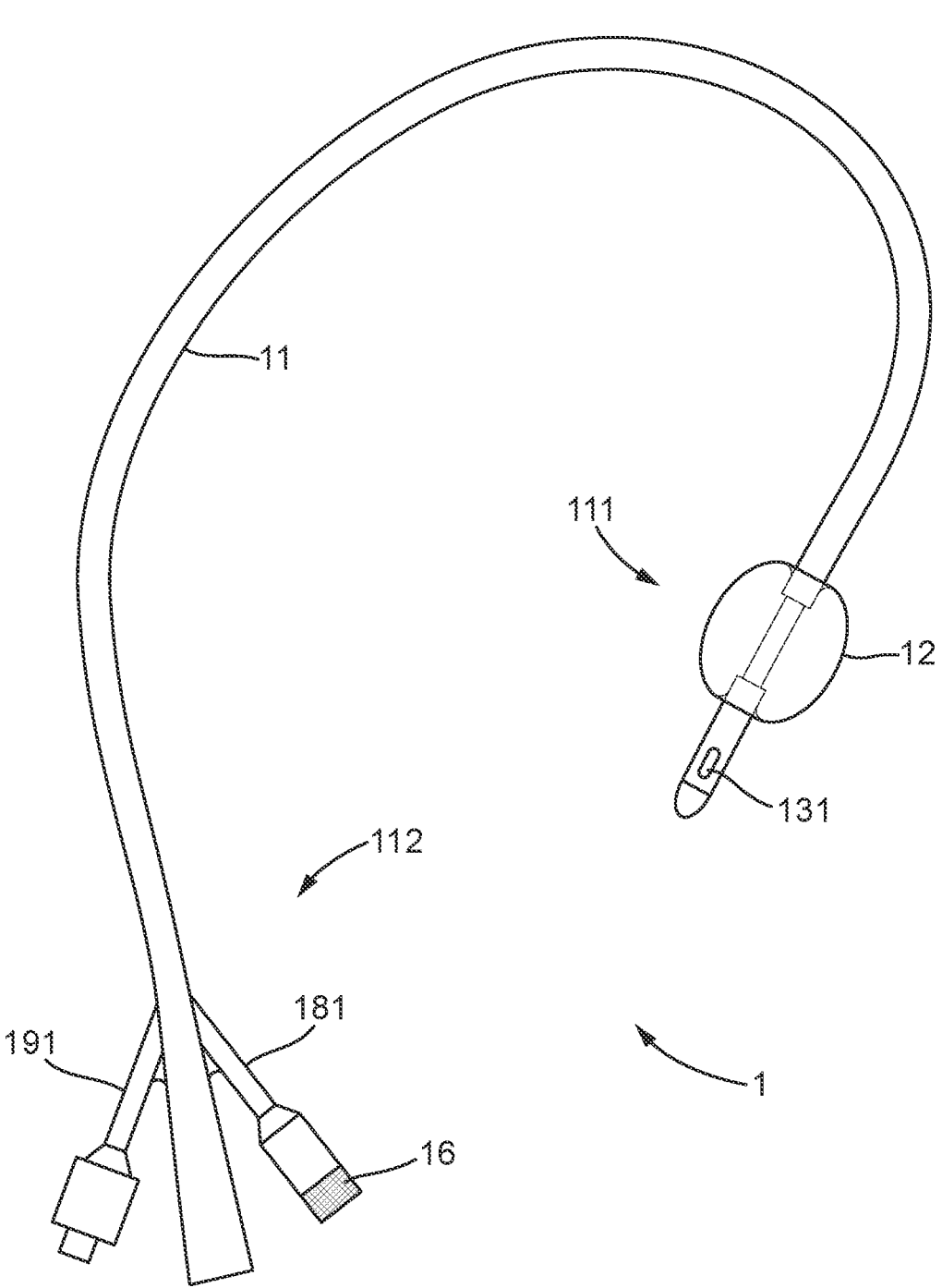
FIG. 1 shows a urinary catheter.

FIG. 1 shows a catheter that may be used in urology. The catheter may be used as an indwelling catheter, intermittent catheter, or a supra-pubic catheter. As shown, the catheter 1 has an elongate body 11. The elongate body 11 has a distal portion 111 and proximal portion 112. The distal portion 111 may be inserted into the patient's body. At least a part of the distal portion 111 may be inserted into the bladder of a patient and may reside there for an amount of time. The amount of time depends on the patient's needs. In the case of an indwelling urinary catheter, the catheter 1 may reside in the patient's body for several months, such as up to three months.

The proximal portion 112 may be left outside the body of the patient. The distal portion 111 may be inserted into the bladder through the urethra, as in the case of indwelling and intermittent catheters, or through a hole provided in the bladder wall and the skin in the pubic region, as in the case of supra-pubic catheters.

The elongate body 11 may have a generally circular transverse cross-section. The elongate body 11 may have a French Gauge suitable for the application. For example, French Gauge sizes 12, 14, 16 and 18 (3.0, 3.7, 5.3 and 6.0 mm respectively) may be used. The catheter may be used in a male patient or a female patient. Due to differences in anatomy, the catheter may be longer for male patients and shorter for female patients. For example, catheters for male patients may be 40 to 55 cm in length, such as 46 cm in length. Catheters for female patients may be 20 to 30 cm, such as 25 cm in length.

The catheter 1 may be made of a flexible and elastic material, such as various rubber materials. For example, the catheter 1 may be made of latex. Instead of latex, silicone, polyurethane or polytetrafluoroethylene may be used. A hydrogel coating may be employed. In particular, silicone may be used to prevent anaphylactic shock for patients with latex allergies. Furthermore, silicone may be more resistant to adherence of bacteria, viruses, prions and fungi and formation of biofilm than latex. Compared with latex, the use of silicone may allow the material of the catheter 1, especially the elongate body 11, to be made thinner, and may allow any internal cavities or lumens to be made larger for the same catheter gauge. Furthermore, the silicone material, and hence any part of the resulting catheter 1 made of the silicone material, may be transparent. If a material other than silicone is used, that material may also be transparent.

The catheter 1 may include a radio-opaque line and/or tip to allow for visualisation by X-ray. In an arrangement, only the tip is radio-opaque, or a radio-opaque line is used which is invisible to the naked eye, at least prior to X-ray, so as to not interfere with the transmission of light.

Figure 2:
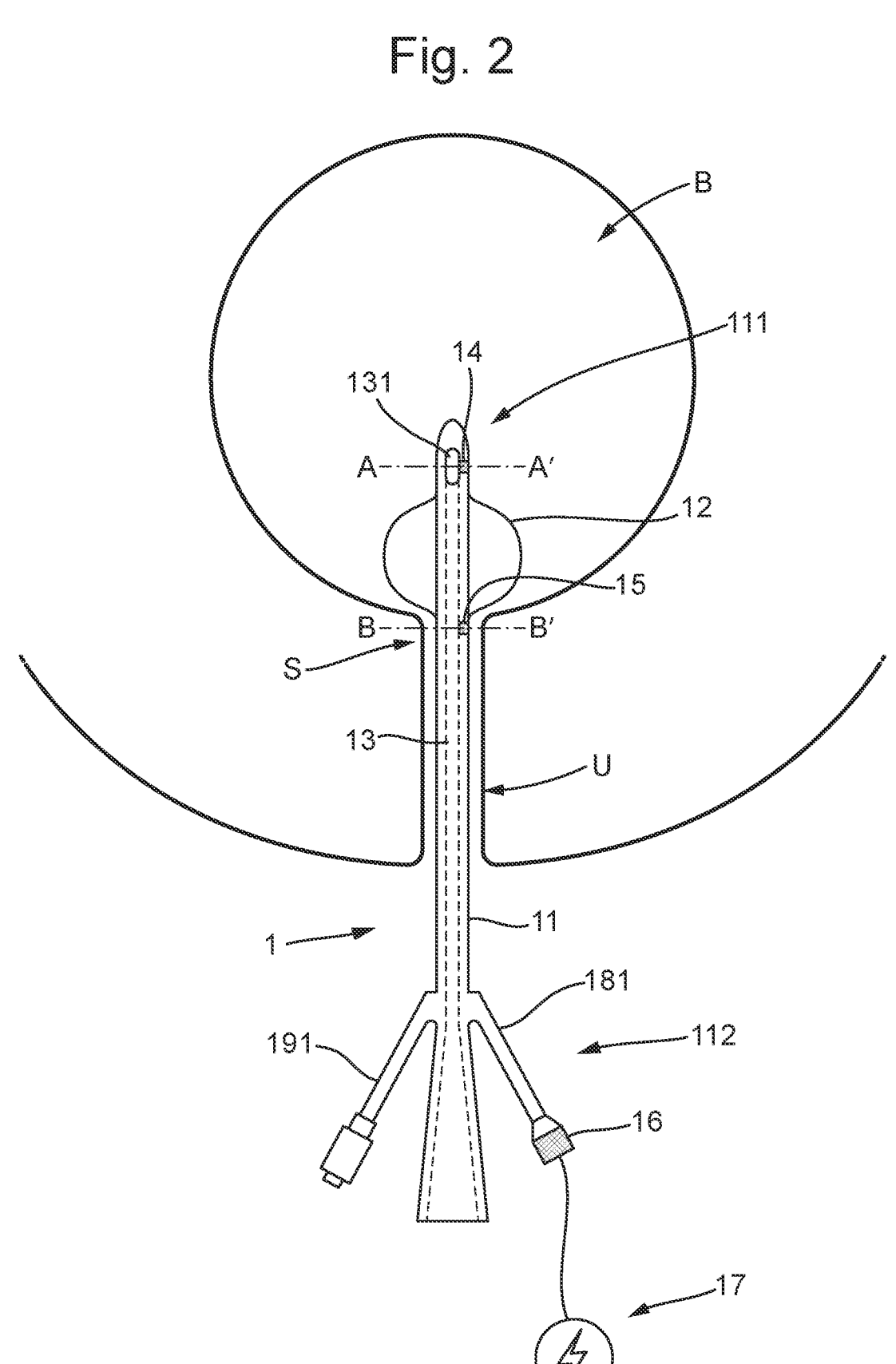
FIG. 2 is a representation of a urinary catheter inserted into the patient's bladder.

As shown in FIG. 2, the catheter 1 has an internal lumen 13 provided within the elongate body 11. The internal lumen 13 may extend from the proximal portion 112 to the distal portion 111. The internal lumen 13 may be in communication with the exterior of the catheter 1 through a fluid port 131.

When inserted, the distal portion 111 may at least partially reside in the bladder B. The remaining length of the distal proton 111 may reside in another part of the patient's body. For example, in the case of an indwelling catheter, the distal portion 111 may partially reside in the urethra U. In the case of a supra-pubic catheter, the distal portion 111 may partially reside in the bladder wall and the skin of the pubic region of the patient's body When the distal portion 111 of the catheter 1 is inserted into the patient's body and at least partially into the bladder B, the fluid port 131 may be within the bladder B. A fluid communication path may thus be formed between the internal volume of the bladder B and the exterior of the patient through the fluid port 131 and the internal lumen 13. Therefore, fluid in the bladder B may be drained out of the patient's body through the internal lumen 13. Alternatively, fluid may be delivered into the bladder B through the internal lumen 13 as required. For example, a clean saline solution and/or an antibiotic solution may be delivered into the bladder B to flush out the bladder B.

The internal lumen 13 may have an internal diameter as required. A larger diameter may generally provide a less resistant flow of fluid, and may be less prone to blockage. As noted above, using silicone may allow the material of the catheter 1 to be made thinner. This may allow a relatively large internal lumen 13 to be provided within the elongate body 11. Similarly, the fluid port 131 may also be made larger, thereby reducing the likelihood of the fluid port 131 being blocked by debris.

As shown in FIG. 2, the catheter 1 may be provided with at least one light generator 14, 15. The at least one light generator 14, 15 may be provided within the distal portion 111 of the elongate body 11. The at least one light generator 14, 15 is configured to generate and emit sterilising light. The sterilising light may be capable of killing bacteria and/or fungi or inhibiting the replication and mobility of bacteria and/or fungi and/or slowing the formation of biofilms. The sterilising light may have similar effects on viruses and/or prions. It should be understood that the at least one light generator 14, 15 may emit, in addition to the sterilising light, radiation that does not have a sterilising effect, so long as the sterilising light generated is suitable and sufficient for killing bacteria, viruses, prions or fungi or inhibiting the replication and mobility of bacteria, viruses, prions or fungi or slowing the formation of biofilms.

As can be seen in FIG. 2, sterilising light is provided in situ, i.e. generated by the at least one light generator 14, 15 in areas where the sterilising light is needed. As found by the present inventor, this arrangement is more efficient than arrangements in which light is delivered by a fibre optic provided within the elongate body. As noted above, when a fibre optic is used this way, the overall optical efficiency is typically around 10% and typically not more than 16.2%. As found by the present inventor, this poor optical efficiency may be due to a number of factors, including absorption by the fibre material, scattering, bending losses and coupling losses. By contrast, by generating the sterilising light directly where it is needed, these losses may be avoided or significantly reduced. As such, a general improvement in energy efficiency may be observed.

The light emitted by the at least one light generator 14, 15 may be blue or violet. Specifically, the light emitted by the at least one light generator 14, 15 may appear blue or violet to the eye. Blue or violet light has been shown to have an ability to kill bacteria forming on a surface. A comparable ability to kill or otherwise inhibit viruses, prions and fungi can be expected. The light generated by the at least one light generator 14, 15 may comprise electromagnetic radiation within a spectral range of 350 to 900 nm, preferably 375 to 600 nm, more preferably 390 to 500 nm.

As found by the inventor, this range of wavelengths provides good antimicrobial properties for the urinary catheter 1. Visible light with a wavelength above 400 nm, such as visible blue or violet light, may kill bacteria on its own without the need for a separate agent such as a photosensitiser or photodynamic agent, as employed in photodynamic therapy. Such visible light, such as 405 nm light, may itself stimulate endogenous photosensitive elements within bacteria, causing them to produce levels of Reactive Oxygen Species (ROS) which then kill the bacterial cell. Such a mechanism may render bacterial cells and other pathogens more susceptible than human cells to killing or inactivation by visible light. Therefore, light, such as visible blue or violet light, up to a certain intensity and overall amount of energy, may be used on its own to inhibit the negative effect of pathogens without significantly damaging human cells.

It has been found by laboratory tests that effective killing of *Escherichia coli* DH5α, *Escherichia coli* K12 and *Proteus mirabilis* may be achieved with visible light. It has been found that six hours of irradiation with 0.16 mW/mm$^2$ of 405 nm light killed a mixture of five species including:

*Escherichia coli* (strain NCIMB 8545), a gram-negative bacteria

*Staphylococcus epidermdiis* (strain NCIMB 12721), a gram-positive bacteria

*Enterococcus faecalis* (strain ATCC 29212), a gram-positive bacteria

*Pseudomonas aeruginosa* (strain NCIMB 10421), a gram-negative bacteria

*Candida albicans* (strain ATCC 10259), a yeast.

Prior to irradiation, a 100 µl aliquot of mixed inoculum was spread across a TSA plate which contained a concentration of each of the five species between $2.4×10^6$ and $3.7×10^6$ CFU mL$^{-1}$.

Although the light generated by the at least one light generator 14, 15 may include radiation that does not have a sterilising effect, the power of any non-sterilising radiation may be kept low, so as to increase the proportion of electrical power used to generate radiation that has a sterilising effect. For example, the total power of the radiation within the preferred spectral range (e.g. the range of 390 to 500 nm) may be at least 50% of the total power of the light generated by the at least one light generator 14, 15. More preferably at least 65% of the power may be located within the preferred spectral range and, more preferably still, at least 80% of the power is located in the preferred spectral range. In a particularly notable embodiment, the total power of the radiation within the range of 390 to 500 nm is at least 80% of the total power of the light generated by the at least one light generator 14, 15. The at least one light generator 14, 15 may further be configured to generate radiation only within the preferred spectral range (e.g. only at 390 to 500 nm, with no other wavelengths present).

Any suitable light generating element may be used to construct the at least one light generator 14, 15 as long as they produce sufficient sterilising light and are compact enough to be provided within the catheter 1. For example, electroluminescent materials may be used. More particularly, light-emitting diode (LED), including organic light-emitting diodes (OLEDs) may be used. Suitable LEDs are commercially available on the market, such as from LUMILEDS in the United States. The LEDs may be powered at 30 mA-60 mA, for example at 30 mA, at 40 mA, at 50 mA or at 60 mA. Alternatively or additionally, multiple mini or micro LEDs and/or LEDs enhanced with quantum dots may be used.

As noted above, a transparent silicone may be used to produce the catheter 1. A transparent material may allow sterilising light generated by the at least one light generator 14, 15 to be transmitted through the material of the elongate body 11 more efficiently. As such, compared with a less optically transparent material, a lower power of light generated by the at least one light generator 14, 15 may be provided without leading to an insufficient power of sterilising light on the surfaces of the elongate body 11. For example, the transparent silicone may have a transmission rate of the sterilising light of at least 80%, at least 85% or at least 90%. If a less transparent material is used, such as a translucent material, the sterilising effect of the sterilising light may be maintained by increasing the power of sterilising light generated by the at least one light generator 14, 15.

As noted above, the catheter 1 may include an internal lumen 13 defined by the elongate body 11. The internal lumen 13 may be in fluid communication with the exterior of the elongate body 11 through a fluid port 131. The fluid port 131 may be located in the distal portion 111. Specifically, the fluid port 131 may be located in the section of the distal portion 111 which will be inserted into the bladder B. Therefore, fluid, particularly urine, in the bladder B may be drained out of the patient's body through the fluid port 131 and through the internal lumen 13 to the proximal portion 112 of the catheter 1. The drained fluid may exit the catheter 1 and be collected, such as in a urine bag.

When the catheter 1 is residing in the patient's body, there is a risk that bacteria and other pathogens from the exterior may propagate through the internal lumen 13, through the fluid port 131, and eventually into the bladder B, thereby causing infections. There is also a risk that pathogens may propagate along the exterior surface of the elongate body 11.

In order to prevent or deter bacteria, viruses, prions and/or fungi from propagating through the fluid port 131, the at least one light generator 14, 15 may comprise a distal light generator 14 positioned to irradiate the fluid port 131. The distal light generator 14 may be positioned close to, or in the vicinity of, the fluid port 131. The distal light generator 14 may at least partially overlap with the fluid port 131 in the longitudinal direction of the elongate body 11. It may be sufficient for the distal light generator 14 to be in the longitudinal vicinity of the fluid port 131. For example, this may be useful due to space restrictions in the vicinity of the fluid port 131.

As shown in FIG. 2, the distal light generator 14 may be co-disposed at the same longitudinal position along the elongate body 11 as the fluid port 131. When the distal light generator 14 and the fluid port 131 are co-disposed at the same longitudinal position along the elongate body 11 as shown, a large proportion of the sterilising light generated by the distal light generator 14 may effectively irradiate the fluid port 131, thereby effectively killing bacteria, viruses, prions or fungi that may form on, in or in the vicinity of the fluid port 131.

Figure 3:
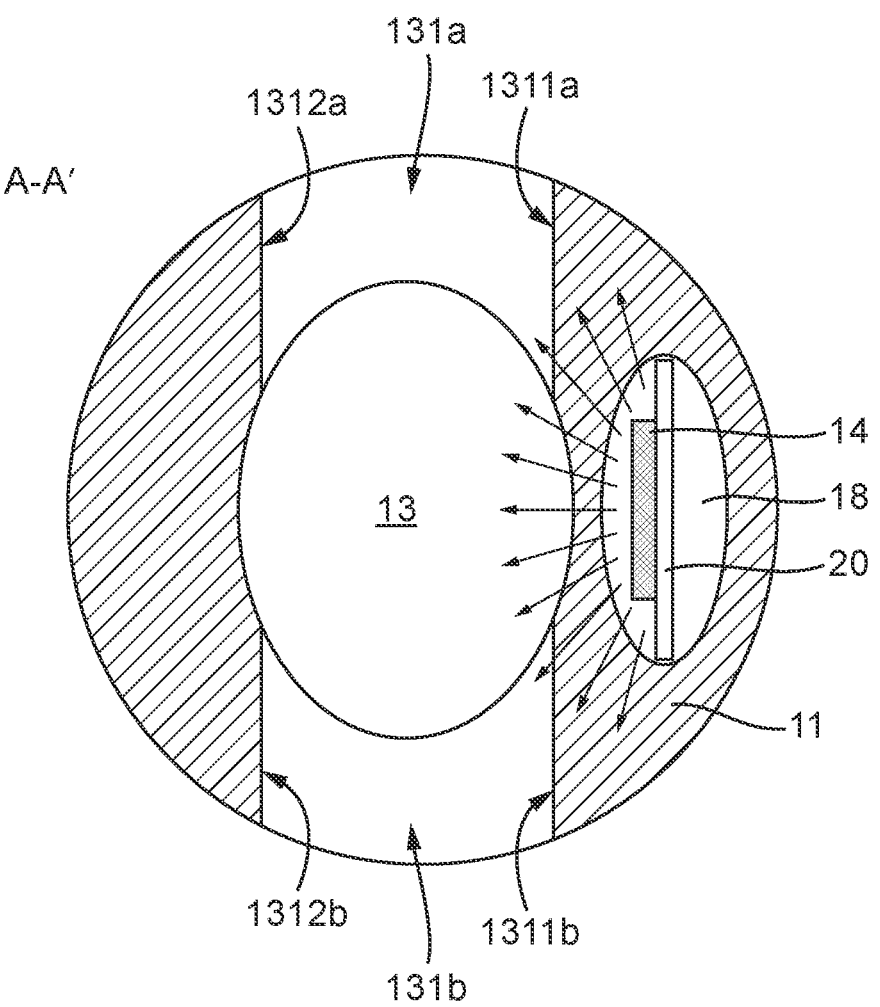
FIG. 3 shows a transverse cross-section of the catheter at the level of the distal light generator.

FIG. 3 shows a transverse cross-section of the elongate body 11 at the level of the distal light generator 14. As shown, the internal lumen 13 may be provided roughly in the centre of the cross-section, and may be in fluid communication with the fluid port 131. The fluid port 131 may comprise several openings. For example, as shown in FIG. 3, the fluid port 131 may comprise two openings 131*a*, 131*b* on either side of the internal lumen 13. As shown, the two openings 131*a* and 131*b* may have approximately the same width as the internal lumen 13. Having two openings 131*a*, 131*b* may allow a larger flow of fluid into the lumen 13. Providing large openings 131*a*, 131*b* may also increase the fluid flow. The two openings 131*a*, 131*b* may be co-disposed at the same longitudinal position along the elongate body 11. In other words, an imaginary line passing through the centres of the two openings 131*a*, 131*b* may be perpendicular to the longitudinal direction of the elongate body 11.

As shown in FIG. 3, the distal light generator 14 may be positioned to be substantially equidistant from the two openings 131*a*, 131*b* of the fluid port 131. This may ensure that both openings 131*a*, 131*b* receive substantially the same amount of sterilising light form the distal light generator 14. It may be beneficial for the two openings 131*a*, 131*b* to receive an equal amount of a sterilising light because the required power of the sterilising light generated by the distal light generator 14 may be minimised. This is because, if one of the openings receives less sterilising light than the other opening, then, in order to ensure that each of the openings 131*a*, 131*b* still receives a sufficient level of sterilising light, it may be useful to compensate by increasing the power of the distal light generator 14, so that the less irradiated opening still receives a sufficient level of sterilising light.

As shown in FIG. 3, each of the two openings 131*a*, 131*b* may be defined by an exposed surface 1311*a*, 1311*b* which is closer to the distal light generator 14, and an exposed surface on the other side 1312*a*, 1312*b* further away from the distal light generator 14. The distal light generator 14 may be powerful enough to maintain a sterilising level of sterilising light at least on the closer exposed surfaces 1311*a*, 1311*b*. The distal light generator 14 may be arranged to maintain a sterilising level of sterilising light covering the entire length (in the longitudinal direction of the elongate body 11) of the openings 131*a*, 131*b*. The distal light generator 14 may be powerful enough to maintain a sterilising level of sterilising light across the openings 131*a*, 131*b*. When the distal portion 111 of the elongate body 11 is inserted into the bladder, the openings 131*a*, 131*b* may be filled with liquid, which may enhance light transmission across the openings across 131*a*, 131*b*. The distal light generator 14 may even be powerful enough to maintain a sterilising level of sterilising light on the exposed surfaces 1312*a*, 1312*b* further away from the distal light generator 14.

Although FIG. 3 shows that the distal light generator 14 comprises a single light generating element, the distal light generator 14 may comprise more than one light generating elements as required. The distal light generator 14 may be an LED. The distal light generator 14 may comprise more than one LED. The LEDs may be powered at 10 mA, 20 mA, 30 mA, 40 mA, 50 mA or 60 mA, for example.

As shown in FIGS. 1 and 2, the catheter 1 may further include a securing member 12. The securing member 12 may be provided on the elongate body 11, such as on the exterior surface of the elongate body 11. The securing member 12 may be provided in the distal portion 111 of the elongate body 11. When the distal portion 111 of the elongate body 11 is inserted into the bladder B of a patient, the securing member 12 may prevent the distal portion 111 from exiting the patient's body. In the case of a supra-pubic catheter, the securing member 12 may abut an internal surface of the bladder B surrounding the hole through which the supra-pubic catheter has been inserted, thereby preventing the supra-pubic catheter from exiting the bladder B. In the case of an indwelling catheter which has been inserted through the urethra U, the securing member 12 may abut the region of the internal surface of the bladder wall surrounding the internal urethral sphincter S, thereby preventing the catheter 1 from exiting the bladder B.

Different forms of securing member 12 may be used. For example, the securing member 12 may comprise deployable mechanical elements which can be expanded once it has been inserted into the bladder B. For example, the securing member 12 may be an inflatable member, such as an inflatable balloon, which can remain uninflated during insertion into the bladder, and can be inflated after it has been inserted into the bladder B.

The elongated body 11 may further define an inflation lumen along its length. The inflation lumen 19 (see FIGS. 6 and 7) may be in fluid communication with the inflatable member. On the proximal side, the inflation lumen 19 may be provided with an inflation port 191 (see FIG. 1, for example). The inflation port 191 may be provided with a valve operable to close or open the inflation lumen 19 to the exterior. To inflate the inflatable member, a fluid may be pumped through the inflation port 191 and the inflation lumen 19, thereby filling the inflatable member with the fluid. Suitable fluids may include water or a saline solution. To deflate the inflation member, fluid in the inflation member may be let out through the inflation lumen 19 and the inflation port 191. The catheter 1 may be a Foley catheter.

In an arrangement, the catheter 1 may have an open tip serving as the fluid port. The catheter 1 may be configured such that the open tip less likely to irritate the patient's bladder. The open tip may extend no further than the most distal surface of the inflatable member. The open tip may terminate within the inflatable member, such as in the centre of the inflatable member. The inflatable member may be situated at the distal tip of the elongate body 11. The inflatable member may surround the open tip serving as a fluid port at the end of the elongate body 11. The catheter 1 may be a catheter of the EZ Care type. Such an open tip arrangement terminating in the centre of the inflatable member may be less likely to irritate the patient's bladder as the inflatable member, when inflated, may prevent the open tip of the catheter 1 from coming into contact with the patient's body. Such a design may increase the distance between the distal light generator 14 and the patient's body, thereby reducing the intensity of heat received by the patient's body.

In more general terms, different catheter tip shapes may be used. For example, the elongate body may end in any type of tip, such as a straight, bent, coude or open tip.

Inflatable members with a large internal volume may be uncomfortable for the patient. Furthermore, in the case of indwelling urinary catheters, which may reside in the patient's bladder for three months or more, the inflatable member may not perfectly deflate and may retain some of the fluid used for inflation. As such, the inflatable member may lead to additional resistance when the catheter 1 is being pulled out of the bladder B, causing discomfort and pain to the patient. As a result, in order to reduce the discomfort and pain endured by the patient, a relatively small inflatable member may be used. For example, the volume of the inflatable member may be no more than 30 ml. The volume of the inflatable member may be no more than 5 ml or no more than 10 ml.

As noted above, there is also a risk that pathogens may propagate along the exterior surface of the elongate body 11. Therefore, as shown in FIG. 2, the at least one light generator 14, 15 may comprise a proximal light generator 15 positioned to irradiate and sterilise a portion of the elongate body 11 on the proximal side of the insertable section of the elongate body 11. In other words, the portion of the elongate body 11 irradiated and sterilised by the proximal light generator 15 may be located somewhere in the patient's body when the catheter 1 has been inserted into the bladder B. For example, the portion of the elongate body 11 irradiated and sterilised by the proximal light generator 15 may be located between the securing member 12 and the internal urethral sphincter S (when the catheter 1 has been inserted into the patient). As the internal urethral sphincter S will generally engage the external surface of the elongate body 11, sterilising light may be prevented from going past the internal urethral sphincter S, through the urethra U and escape to the outside of the patient. Alternatively, the portion of the elongate body 11 irradiated and sterilised by the proximal light generator 15 may be located on the proximal side of the internal urethral sphincter S, such as at least 15 mm away from the sphincter S on the proximal side of the securing member. This may reduce the risk of the proximal light generator 15 being push substantially or even entirely into the bladder B. This may ensure that a sterilising band of light is maintained on the proximal side of the sphincter S, so that bacteria, viruses, prions or fungi may be prevented from travelling or propagating beyond the band of light and eventually into the bladder. Thus, this may help maintain the sterility of the bladder or prevent ingress of new bacteria, viruses, prions or fungi.

The proximal light generator 15 may irradiate and sterilise the exposed area of a portion of the elongate body 11. This may prevent pathogenic growth on the exposed area of the elongate body 11. The exposed area that is irradiated and sterilised by the proximal light generator 15 may be partially in contact with the internal urethral sphincter S. In this arrangement, pathogenic growth on the internal urethral sphincter S and on a region of the bladder B surrounding the internal urethral sphincter S may be effectively prevented or reduced. If the proximal light generator 15 is located to irradiate and sterilise a portion of the elongate body 11 further to the proximal side of the internal urethral sphincter S, then pathogenic growth on the urethra or on the exposed area of the irradiated portion of the elongate body 11 may be prevented.

The proximal light generator 15 may be configured to irradiate and sterilise a complete cylindrical section of the exterior surface of the elongate body. In other words, the proximal light generator 15 may be arranged to create a complete ring of sterilising light. The proximal light generator 15 may be configured such that the intensity of sterilising light as measured at the exterior surface of the elongate body 11 is at least a predetermined intensity threshold throughout the cylindrical section of the exterior surface. The predetermined intensity threshold may be 0.02 to 0.2 mW/mm², for example 0.03, 0.05, 0.08 or 0.10 mW/mm². For the avoidance of doubt, the intensity of sterilising light need not be constant throughout the cylindrical section. In other words, the intensity of the sterilising light may exceed the predetermined intensity threshold at certain points of the exterior surface within the cylindrical section. However, a greater light intensity will result in a greater power consumption, thereby increasing the need for the battery to be replaced or recharged.

The proximal light generator 15 may irradiate and sterilise the interior surface of the internal lumen 13. As above, the proximal light generator 15 may irradiate and sterilise a complete cylindrical section of the interior surface of the internal lumen 13. The proximal light generator 15 may be positioned within the elongate member 11 as described above. Irradiating a complete cylindrical section of the interior surface of the internal lumen 13 may have a similar effect to irradiating the fluid port 131 with the distal light generator 14. In other words, by forming a ring of sterilising light on the interior surface at a position along the internal lumen 13, bacteria and other pathogens originating from the exterior of the patient's body may be killed at the cylindrical section of the interior surface irradiated by the proximal light generator 15. Pathogens forming in the cylindrical section on the interior surface may be killed. The proximal light generator 15 may be powerful enough to provide a sterilising level of sterilising light across the internal lumen 13. In this case, pathogens away from the interior surface (e.g. in the centre of the lumen 13) may also be killed. Bacteria or other pathogens may thus be prevented from propagating further into the internal lumen 13 and reaching the bladder B.

The proximal light generator 15 may irradiate and sterilise mostly or exclusively the interior surface of the internal lumen 13. This may be achieved by orientating the proximal light generator 15 so that the generated light is not aimed substantially outwards from the central axis of the elongate body 11. For example, the proximal light generator 15 may be orientated to aim the generated light towards the central axis of the elongate body 11. Alternatively or additionally, this may be achieved by rending the exterior surface of the elongate body 11 partially or fully opaque to the sterilising light, such as by applying an opaque coating. The opaque coating may absorb and/or reflect the sterilising light. This may help reduce the amount of sterilising light delivered onto the body tissue of the patient. It should be understood that any region of the elongate body 11 may be selectively rendered partially or fully opaque to light of any desired wavelength as required. The coating may alternatively or additionally be configured to reduce the transfer of heat from the light generators to human tissue. Materials or structures with thermally insulating properties may be used for this purpose, such as around the region of any of the light generators.

Even when the fluid is generally still, bacteria and other pathogens may move due to diffusion and/or convection. Therefore, the cylindrical section may be of sufficient length so as to ensure that bacteria, viruses, prions or fungi are thoroughly killed. In particular, the length may be sufficient to ensure that any bacteria, viruses, prions or fungi suspended in the fluid within the internal lumen 13 will dwell long enough in the cylindrical section to be killed. For example, the cylindrical section of the exterior surface of the elongate body 11 or the interior surface of the internal lumen 13 may be at least 1-8 mm long in the longitudinal direction of the elongate body 11. The cylindrical section may be at least 2 mm, 3 mm, 4 mm, 5 mm, or 6 mm long. The properties and/or structure of the catheter wall may be chosen to enhance the distribution of light.

Figure 6:
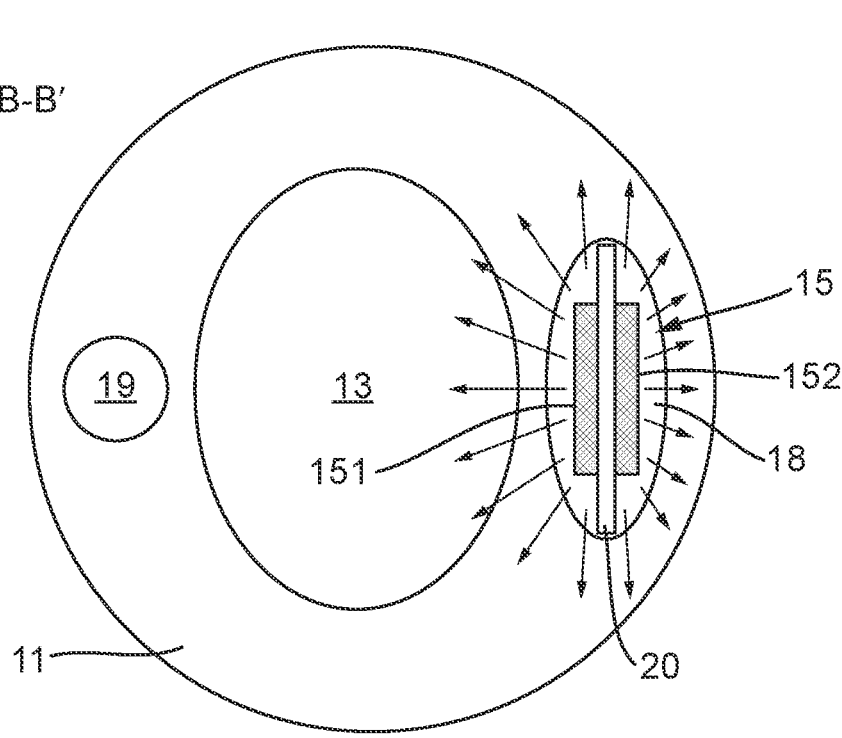
FIG. 6 shows a transverse cross-section of one arrangement of the catheter at the level of the proximal light generator.

The proximal light generator 15 may be implemented with a single light generating element. Alternatively, as shown in FIG. 6, the proximal light generator 15 may comprise first and second light generating elements 151, 152. The first and second light generating elements 151, 152 of the proximal light generator 15 may be arranged to face an opposite direction to each other. This may ensure that a substantially 360° ring of sterilising light is created by the proximal light generator 15. As shown, the first light generating element 151 may generally face a central portion of the elongate body 11, or more specifically the central axis of the elongate body 11. The second light generating element 152 may, as a result, face the exterior surface of the elongate body 11. Light generated by the light generating elements 151, 152 may reflect, refract, and otherwise scatter, within the elongate body 11. The presence of lumens, such as the internal lumen 13, may enhance the distribution of light.

In this arrangement, the internal lumen 13 may be mainly irradiated by the first light generating element 151. In addition, the first light generating element 151 may be configured to generate a greater power of sterilising light than the second light generating element 152. The first light generating element 151 may even be configured to generate about twice as much power of sterilising light as the second light generating element 152. As other light scattering elements (such as the internal lumen 13 and optionally the inflation lumen 19) may be present in the region mainly irradiated by the first light generating element 151, a higher power of sterilising light from the first light generating element 151 may ensure that a required level of sterilising light is maintained throughout the cylindrical section. Less power of sterilising light from the second light generating element 152 may be required because a lesser portion of the elongate body may be irradiated by the second light generating element 152. As noted above, it may be desirable to provide no more sterilising light than necessary so as to reduce the overall power consumption of the at least one light generator 14, 15, and thereby reduce the need to recharge or replace the battery powering the at least one light generator 14, 15. This may also reduce the amount of heat generated.

It should be understood that the disclosure of specific arrangements of light generators herein does not preclude the addition of further light generators placed anywhere on the device, including in a portion of the catheter which is intended to reside outside the patient's body, and these further light generators may emit sterilising and/or non-sterilising light.

The entire external surface, the surface of the internal lumen and/or the cross section of any lumen of the catheter could be illuminated along multiple longitudinal sections. One of these illuminated longitudinal sections may be positioned on either side of the external urinary orifice/ urinary meatus in the case of urethral catheters, or at the entry point of the catheter into the body in the case of supra-pubic placement. Such placement may provide sterilising light to prevent entry of pathogens into the body. Light generating elements of sufficient power may be used to irradiate the area of the body around the entry point of the catheter into the body with sterilising light. Such light may be useful for visual illumination as well as or instead of sterilisation. Illuminating the entry point of the catheter into the body may make it easier to see this region and thus keep it clean. Such illumination may help with earlier identification of blockages or infection. Such illumination may increase awareness of the device, prompting patients and health care workers to keep the area clean and to not accidentally remove the catheter 1. Such illumination may be visible through the skin and may help with placement of the catheter 1.

For example, the catheter 1 may include one or more red-infrared light generator (not separately shown in the figures) configured to emit red and/or infrared light. The red-infrared light generator may be positioned to irradiate an area of a portion of the elongate body on the proximal side of the securing member. The red-infrared light generator may be configured to emit red light within a spectral range of 620 to 700 nm and/or infrared light within a spectral range of 800 to 2500 nm. The red-infrared light generator may be configured to emit only red and/or infrared light, i.e. the light emitted by the red-infrared light generator may consist of radiation within a spectral range 620 to 2500 nm, or 620 to 700 nm, or 800 to 2500 nm.

The red and/or infrared light may provide an anti-inflammatory effect. This may reduce discomfort caused by the catheter 1. For example, by positioning the red-infrared light generator at a suitable distance to the proximal side of the securing member 12, when the catheter 1 is inserted into the patient's body, the red-infrared light generator may be at a position around the entry point into the body. Red and/or infrared light may be irradiated around the entry point. This may be useful, such as in the case of a supra-pubic catheter, because the red and/or infrared light may help suppress inflammation in the region where the catheter 1 traverses the pubic skin and the bladder wall. This may also be useful in the case of a catheter 1 inserted up the urethra because the red and/or infrared light may help suppress inflammation around the urinary orifice/urinary meatus, or in the urethra. The red-infrared light generator may be positioned other than on the proximal side of the securing member 12. For example, the red-infrared light generator may be positioned to help reduce inflammation in the bladder or ureters. Furthermore, in certain cases, the irradiation of red and/or infrared light may prevent or reduce any inflammation where heat or other irritation produced by the irradiation of blue/violet light is found to be a contributing factor.

The catheter 1 may comprise additional light generators (not shown in the figures) configured to emit sterilising light around the point where the catheter 1 enters the body. For example, a sterilising light generator may be positioned such that the portion of the elongate body whose area is irradiated and sterilised by the proximal light generator is, when the distal portion is in the patient's body including the bladder, located at the urinary orifice/urinary meatus, or, in the case of supra pubic catheters, at the point where the catheter 1 traverses the pubic skin and bladder wall. Two or more such sterilising light generators may be provided so that the regions on either side of the entry point to the body are irradiated and sterilised. Alternatively, a single sterilising light generator may be provided to illuminate a length of the elongate body 11 so that the regions on either side of the entry point to the body are irradiated and sterilised. These additional light generators, or any other light generators disclosed herein, may be powerful enough to irradiate and sterilise a region beyond the external surface of the catheter 1. For example, one or more of these light generators, such as one located at or near the distal tip of the catheter or the at least one light generator 14, may irradiate the urine, the interior of the bladder and/or up to and including the patient's tissue such as the epithelium of the urethra and/or the interior surface of up to all of the bladder and the ureters.

The catheter 1 may comprise light generators serving as a visual guide. In this case, the light generators may generate light of any suitable wavelength or wavelengths. For example, white light may be used. This light may be active during insertion or removal of the catheter 1 and may be visible through the patient's body so as to act as a guide light for placement of the catheter.

In an arrangement, the first and second light generating elements 151, 152 may be LEDs. The LEDs may be powered at 10 mA, 20 mA, 30 mA, 40 mA, 50 mA or 60 mA, for example. The first light generating element 151 may be powered at 60 mA. The second light generating element 152 may be powered at 30 mA.

As with the at least one light generator 14, 15, the red-infrared light generator may comprise one or more similar light generating element, which may also be an LED.

Depending on a given patient's particularities, it may be desirable to limit the dose of sterilising light, even if it is all within the visible spectrum. This is because an excessive dose of sterilising light may in certain cases cause excessive damage to human cells. In particular, it may be desirable to ensure the intensity and/or duration and/or overall energy of sterilising light are kept below certain thresholds. For instance, it may be desirable to keep peak intensity below $0.15 \text{ mW/mm}^2$ and/or the duration of continuous illumination below 1 hour. This may result in less than $0.54 \text{ J/mm}^2$ of energy being delivered during a given period of illumination.

In an arrangement, the securing member 12 may be an inflatable member, and the proximal light generator 15 may irradiate and sterilise a complete cylindrical section of the exterior surface of the elongate body 11. In this case, the proximal light generator 15 may be located such that the centre point of the cylindrical section may be approximately 3-9 mm (e.g. 6 mm) from the inflatable member, measured from the point where the inflatable member meets the (non-inflatable) exterior surface of the elongate body 11 on the proximal side. As found by the inventor, this may ensure that at least a part of the cylindrical section irradiated and sterilised by the proximal light generator 15 will be situated between the inflatable member and the internal urethral sphincter S when the catheter 1 has been inserted into the bladder B.

Alternatively, the proximal light generator 15 may be located such that the centre point of the cylindrical section may be approximately 10-20 mm (e.g. 15 mm) from the inflatable member, measured from the point where the inflatable member meets the (non-inflatable) exterior surface of the elongate body 11 on the proximal side. As found by the inventor, this may ensure that the cylindrical section irradiated and sterilised by the proximal light generator 15 will be at least partially outside the bladder even if the catheter 1 shifts further into the bladder B.

Although only one proximal light generator 15 is shown in the Figures, it should be understood that multiple proximal light generators may be provided. For example, one proximal light generators may be provided at 3-9 mm from the inflatable member as discussed above, and another may be provided at 10-20 mm from the inflatable member as discussed above.

Although FIG. 6 shows that first and second light generating elements 151, 152 are provided, the proximal light generator 15 may comprise more than two light generating elements. For example, a circular array of LEDs may be provided on a transverse cross-section of the elongate body 11. Similarly, although FIG. 3 shows only one light generating element for the distal light generator 14, it should be understood that the distal light generator 14 may comprise more than one light generating element. For example, two or more LEDs may be used.

In general, any light generator disclosed herein may be implemented using any number of light generating elements. Furthermore, when several light generating elements are used to implement a light generator, the light generating elements may produce light at the same or different intensities, of the same or different wavelengths, and may be selectively activated at the same or different times and/or for the same or different durations.

It should be noted that the sufficient sterilising effect may be achieved by providing one or the other of the distal and proximal light generators 14, 15 disclosed above. However, if both the distal and proximal light generators 14, 15 are present, this may have the added benefit that the distal light generator 14 serves as a second line of defence in addition to the proximal light generator 15. In other words, any pathogens that are not killed or sufficiently inhibited by the sterilising light from the proximal light generator 15 may, as they travel further to the fluid port 131, be killed or inhibited by the sterilising light from the distal light generator 14.

The elongate body 11 may further define an elongate lighting cavity 18. As shown in FIGS. 3 and 6, the at least one light generator 14, 15 may be provided within the elongate lighting cavity 18. For the avoidance of doubt, the term "cavity" does not necessarily imply that there should be any empty space left in the cavity after the at least one light generator 14, 15 has been provided within the elongate body 11. In other words, the elongate lighting cavity 18 may be completely filled by the at least one light generator 14, 15. Depending on the manufacturing method and detailed design, the elongate lighting cavity 18 may include some empty space around the at least one light generator 14, 15.

The elongate lighting cavity 18 may restrict any translation and/or rotation of the at least one light generator 14, 15 relative to the elongate body 11. For example, the restriction of rotation may be accomplished by providing the elongate lighting cavity as a non-circular shape. In other words, the elongate lighting cavity 18 may have a non-circular transverse cross-section, as shown in FIGS. 3 and 6. As can be seen, due to the non-circular transverse cross-section, the at least one light generator 14, 15 may rotate within the elongate lighting cavity 18 only through a small range of angles before meeting any resistance.

The at least one light generator 14, 15 may be provided on a flexible printed circuit board 20. As shown in FIGS. 3 and 6, the flexible printed circuit board may be wider than the at least one light generator 14, 15, so that the flexible printed circuit board 20 interacts with the internal surface of the elongate lighting cavity 18. In other words, the elongate lighting cavity 18 may be shaped and/or dimensioned to restrict any rotation of the flexible printed circuit board 20 provided within the elongate lighting cavity application. The flexible printed circuit board 20 may have a width of less than 1-3 mm, e.g. less than 2 mm. The flexible printed circuit board 20 may have a sufficient length to span the distance between the distal 14 and proximal 15 light generators. For example, the distal 14 and proximal 15 light generators may be about 3-11 cm apart, e.g. about 7 cm apart.

For further security, the elongate lighting cavity may be dimensioned to maintain a compressive force on the flexible printed circuit board 20. In other words, the elongate lighting cavity 18 may be slightly undersized, and the flexible printed circuit board 20 may be slightly bent. This may create a frictional force existing between the flexible printed circuit board 20 and the internal surface of the elongate lighting cavity 18. This frictional force may restrict the translation and/or rotation of the flexible printed circuit board 20 within the elongate lighting cavity 18.

As noted above, there need not be any empty space left in the elongate lighting cavity 18 after the at least one light generator 14, 15 (and the flexible printed circuit board 20) has been provided within the elongate body 11. In this case, the elongate lighting cavity 18 may precisely follow the contour of the at least one light generator 14, 15 (and the flexible printed circuit board 20), thereby providing a high degree of restriction of translation (particularly in the longitudinal direction) and rotation of the at least one light generator 14, 15.

The elongate lighting cavity 18 may be part of a lighting lumen extending between the proximal portion 112 and the distal portion 111 of the elongate body 11. This arrangement may facilitate the provision of the at least one light generator 14, 15 within the elongate lighting cavity 18. As shown in FIGS. 1 and 2, the catheter 1 may be provided with a lighting port 181, and the lighting lumen may extend into the lighting port 181. The at least one light generator 14, 15 may then be shifted along the lighting lumen towards the distal portion 111 until it reaches the elongate lighting cavity 18.

Figure 4:
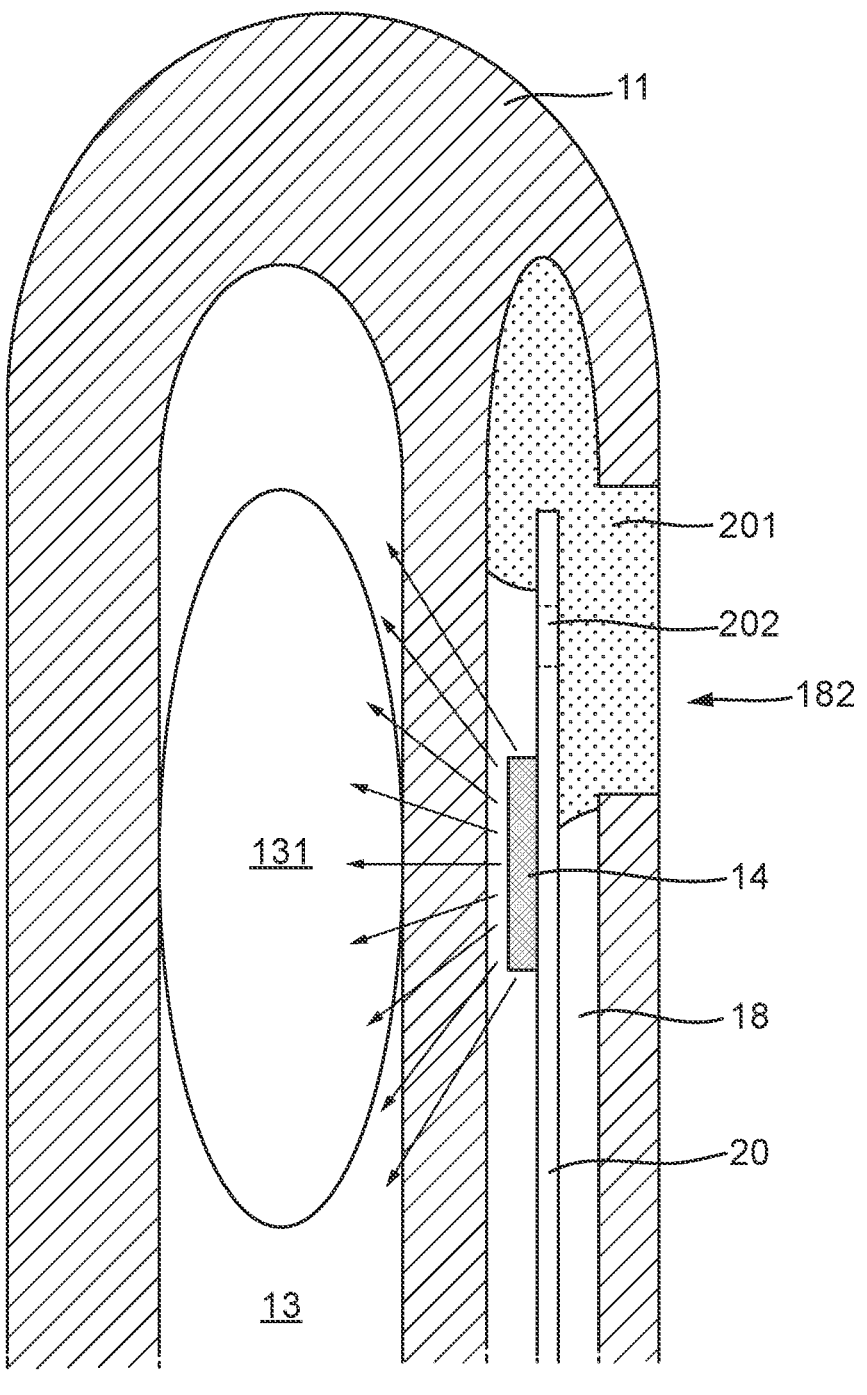
FIG. 4 shows the longitudinal cross-section of the catheter at the level of the distal light generator.

The following method for producing a catheter, optionally a catheter 1 as descried above, may be used. The method may comprise providing a catheter comprising an elongate body 11 having a distal portion 111 and a proximal portion 112, initially without any light generator. The elongate body 11 may, as discussed above, define an internal lumen 13 and a lighting lumen. The elongate lighting cavity 18 may be part of the lighting lumen. Initially, both the internal lumen 13 and the lighting lumen may be in fluid communication with the exterior of the elongate body 11 respectively through the fluid port 131 and the lighting opening 182. The lighting opening 182 may allow access from the exterior into the elongate lighting cavity 18. As shown in FIG. 4, both the fluid port 131 and the lighting opening 182 may be located in the distal portion 111.

At least one light generator 14, 15 may then be provided. The at least one light generator 14, 15 may be inserted into the elongate lighting cavity 18, which may be part of the lighting lumen at the distal portion 111. The at least one light generator 14, 15 may be inserted into the lighting lumen at the proximal portion 112 of the elongate body 11. The at least one light generator 14, 15 may then be shifted along the lighting lumen towards the distal portion 111 until it reaches the elongate lighting cavity 18.

As noted above, the at least one light generator 14, 15 may be provided on a flexible printed circuit board 20. The flexible printed circuit board 20 may be further provided with a through hole 202 near the distal tip of the printed circuit board 20. As such, in order to insert the flexible printed circuit board 20 into the elongate lighting cavity 18, the flexible printed circuit board 20 may first be inserted into the lighting lumen using the lighting port 181, and then drawn though the lighting lumen by means of a string or a wire attached to the through hole 202 until it reaches the required position within the elongate lighting cavity 18. The wire may be provided with a hook to engage the through hole 202.

Alternatively or additionally, the flexible printed circuit board 20 may be inserted into the elongate lighting cavity 18 by providing a jet of compressed air into the lighting lumen. The flexible printed circuit board 20 may be inserted into the elongate lighting cavity 18 from the distal side through the lighting opening 182, and the jet of compressed air may be provided from the distal side. Alternatively, the flexible printed circuit board 20 may be inserted into the elongate lighting cavity 18 from the proximal side, and the jet of compressed air may be provided from the proximal side.

After the flexible printed circuit board 20 together with the at least one light generator 14, 15 has been placed in the elongate lighting cavity 18, the wire or string used to draw the flexible printed circuit board 20 through the lighting lumen may be detached or cut off, and the lighting opening 182 may be sealed, so as to close it.

Figure 5:
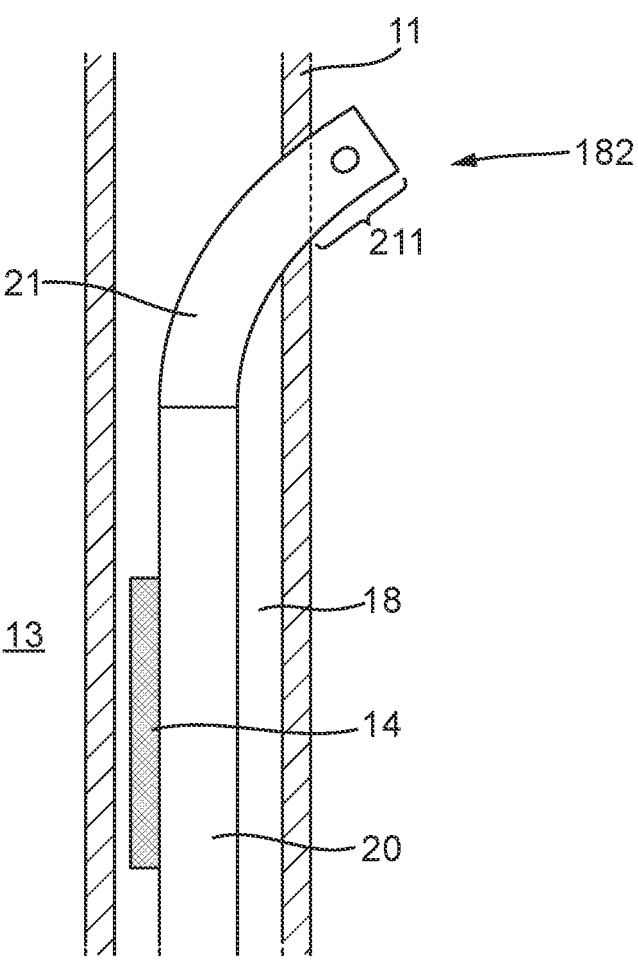
FIG. 5 shows another longitudinal cross-section of the catheter at the level of the distal light generator.

Alternatively, as shown in FIG. 5, the flexible printed circuit board 20 may be provided with a capping member 21. The capping member 21 may be made of an elastic material, such as silicone rubber. The capping member 21 may have a through hole. The capping member 21, together with the flexible printed circuit board 20, may be drawn through the lighting lumen by means of a string or a wire attached to the through hole of the capping member 21 until the capping member 21 partially protrudes out of the lighting opening 182 and until the at least one light generator 14, 15 reaches the required position within the elongate lighting cavity 18. The protruding portion 211 of the capping member 21 may then be cut off. The protruding portion 211 may be cut off substantially flush with the exterior surface of the elongate body 11. Afterwards, any gap left around the capping member 21 in the lighting opening 182 may be sealed, so as to close it.

Sealing the lighting opening 182 may prevent fluid in the bladder B from entering the elongate lighting cavity 18, and thereby interfering with the operation of the at least one light generator 14, 15. As the fluid in the bladder B may be ionic, if the fluid is allowed to enter the elongate lighting cavity 18, it may cause short-circuiting, potentially damaging the at least one light generator 14, 15. The sealing step is however optional, as light generators able to function when submersed may be used. For example, the at least one light generator 14, 15 may be enclosed in a liquid-proof enclosure prior to insertion into the elongate lighting cavity 18. For example, any exposed conductive parts of the light generators 14, 15 may be potted in, preferably with a transparent potting material, prior to insertion into the elongate lighting cavity 18.

The sealing of the lighting opening 182 may be achieved by injecting a sealant 201 over and/or into the lighting opening 182. In addition to sealing and closing the lighting opening 182, the sealant 201 may also fix the at least one light generator 14, 15 in place. As shown in FIG. 4, to close the lighting opening 182, a sealant 201 may be injected into the lighting lumen 182. Sufficient sealant 201 may be injected so that the sealant 201 reaches the flexible printed circuit board 20 and/or the at least one light generator 14, 15. The sealant 201 may bond with the material of the elongate body 11 and/or the at least one light generator 14, 15 and/or the flexible printed circuit board 20. The bonding may help fix the at least one light generator 14, 15 in place within the elongate lighting cavity 18. This may have the effect of substantially eliminating any translation and/or rotation of the at least one light generator 14, 15, thereby ensuring that the relevant surfaces of the elongate body 11 are properly irradiated and sterilised by the at least one light generator 14, 15.

The sealant 201 may be a mixture of one or more solutions. For example, an acrylate adhesive such as Loctite Superglue Acrylate Adhesive may be used as well as an acrylate primer such as Loctite Acrylate Primer. The lighting opening 182 may alternatively be closed through other means, such as by melting the material of the catheter or by otherwise applying heat, electricity, light, UV curing or other chemicals. Any combination of these methods may be used with or without a sealant 201.

Figure 7:
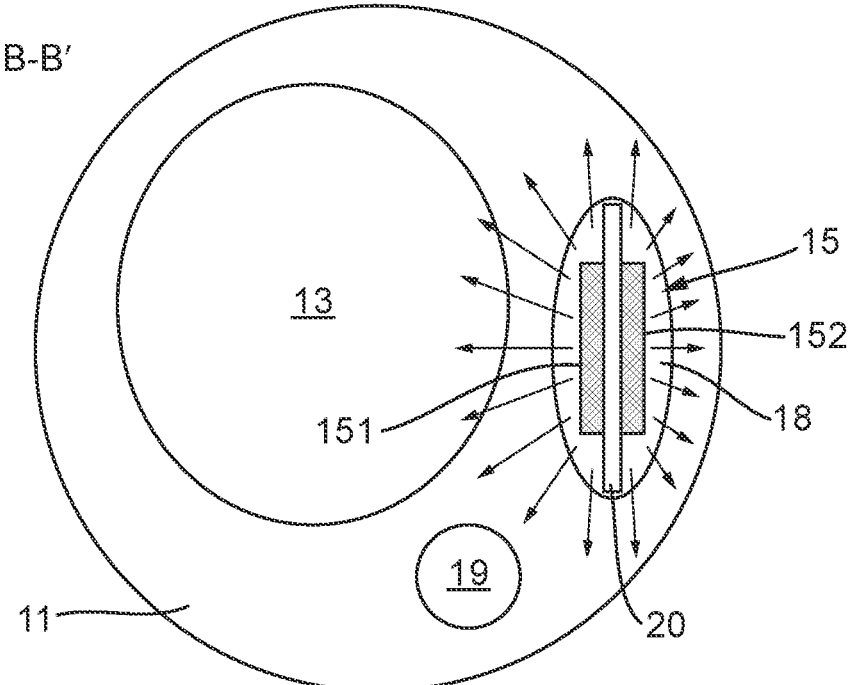
FIG. 7 shows a transverse cross-section of another arrangement of the catheter at the level of the proximal light generator.

Although FIG. 6 shows a particular arrangement of the internal lumen 13, the inflation lumen 19 and the lighting cavity 18, in which the internal lumen 13 is provided generally between the inflation lumen 19 and the elongate lighting cavity 18, this is not the only suitable arrangement. The arrangement of the lumens and the elongate lighting cavity 18 within the transverse cross-section of the elongate body 11 is not particularly critical. For example, as shown in FIG. 7, the elongate lighting cavity 18 and the inflation lumen 19 may be provided substantially on one side of the cross-section, and the internal lumen 13 may be provided on the other side. For the avoidance of doubt, the shapes of the lumens, 13, 19 and elongate lighting cavity 18 are not necessarily in the shape as shown in FIGS. 6 and 7. They may be in any suitable shape, including non-circular and non-elliptical shapes. For example, one or more of the lumens 13, 19 and/or the elongate lighting cavity 18 may have a semi-lunar or semi-circular shape.

Although not shown in the figures, electrical power may be provided to the at least one light generator 14, 15 by electrical wiring. The electrical wiring may be provided within the lighting lumen. Two electric wires may be provided to connect the positive and negative electrical terminals of the at least one light generator 14, 15 respectively to the positive and negative terminals of the power source. The electrical wiring may be connected to the flexible printed circuit board 20. On the proximal side of the elongate body 11, the electrical wiring may extend into the lighting port 181, and may be connected to an electrical connector 16.

A third electric wire may be provided in the lighting lumen. The third electric wire may also be connected to the flexible printed circuit board 20 and the electrical connector 16. The third electric wire may serve as a means of detecting that the catheter 1 has been connected to the power source. Specifically, the third electric wire, together with one of the other two electric wires, may close a circuit when the power connector 16 is connected to the power source. The three electric wires may be arranged substantially side by side within the lighting lumen.

Alternatively, instead of providing electrical wiring, the flexible printed circuit board 20 may be extended all the way through the lighting lumen, through the lighting port 181, and up to the power connector 16. Using a long flexible printed circuit board 20 instead of electrical wiring may simplify the manufacturing process because there is no need to connect electrical wiring onto the flexible printed circuit board 20. Furthermore, such a long flexible printed circuit board 20 may have sufficient rigidity to be pushed into the lighting lumen from the proximal side until the at least one light generator 14, 15 reaches the final position in the elongate lighting cavity 18, without the aid of a pulling wire or compressed air, as mentioned above.

The catheter 1 may comprise one or more light sensors. The one or more light sensors may be provided to control the illumination of at least one of the light generating elements. Although it may be recommended that health care staff do not switch on the sterilising light of the catheter before inserting it into the patient, some may still do so either inadvertently or to test whether the light works. If the catheter is switched on while it is outside the body, there may be a risk that the light may be held too close to their eye, causing discomfort or even damage to vision. The provision of light sensors may address this issue.

For instance, once all of the one or more light sensors do not detect ambient light, such as when the catheter is inserted into the body, the light generating elements of the catheter may be activated. The one or more light sensors may be positioned on the flexible printed circuit board 20 in the distal portion 111 of the elongate body 11. The one or more light sensor may be sufficient in number and be positioned so as to prevent an individual from covering all of them with their fingers. The one or more light sensors may be configured to be non-sensitive to certain wavelengths of light, especially blue light, such that turning on the one or more light generator 14, 15 would not trigger the one or more sensors to turn the one or more light generator 14, 15 off. The one or more light sensor may be selectively sensitive only to wavelengths of light not produced by any of the light generating elements of the catheter 1. The one or more light sensors may be positioned so as to limit the amount of light generated by the light generating elements of the catheter 1 reaching the light sensors when the catheter is within the body.

As noted above, the at least one lighting generator 14, 15 may be powered by an external power source, such as a battery 17. As shown in FIG. 2, the battery 17 may be connected to the power connector 16. The power connector 16 may be secure enough to prevent inadvertent disconnection of the battery 17.

However, the force required to disconnect the battery 17 at the power connector 16 may optionally not be excessive. An excessive disconnection force may be dangerous. For example, if the battery 17 is being forcefully pulled, or if the electrical cable of the battery 17 is caught, and if the power connector 16 has a large disconnection force, the disconnection force may be sufficient to pull the catheter 1 out of the patient's body. This may be especially dangerous if the securing member 12 has been deployed, such as when the inflatable member is inflated, because forcefully pulling the securing member 12 out past the internal urethral sphincter S and through the urethra U (or through the bladder wall and the pubic skin in the case of a supra-pubic catheter) may cause severe injuries to the patient. Therefore, the disconnection force of the power connector 16 may be limited so that the power connector 16 will disconnect instead of causing the catheter 1 to be forcefully pulled out of the patient. The disconnection force of the power connector 16 may be less than a force required to disconnect the catheter 1 from a urine bag connected to the catheter 1. For example, the disconnection force of the power connector 16 may be about 6 Newtons. The force for disconnecting the catheter 1 from the urine bag may be about 42 Newtons.

Power connector 16 may be fixed into lighting port 181 with a glue or another sealant. Alternatively, the power connector 16 may be held in lighting port 181 by friction. Heat may be applied during manufacture in order to shrink lighting port 181 around the power connector 16. The seal formed between power connector 16 and lighting port 181 may be waterproof.

Figure 8:
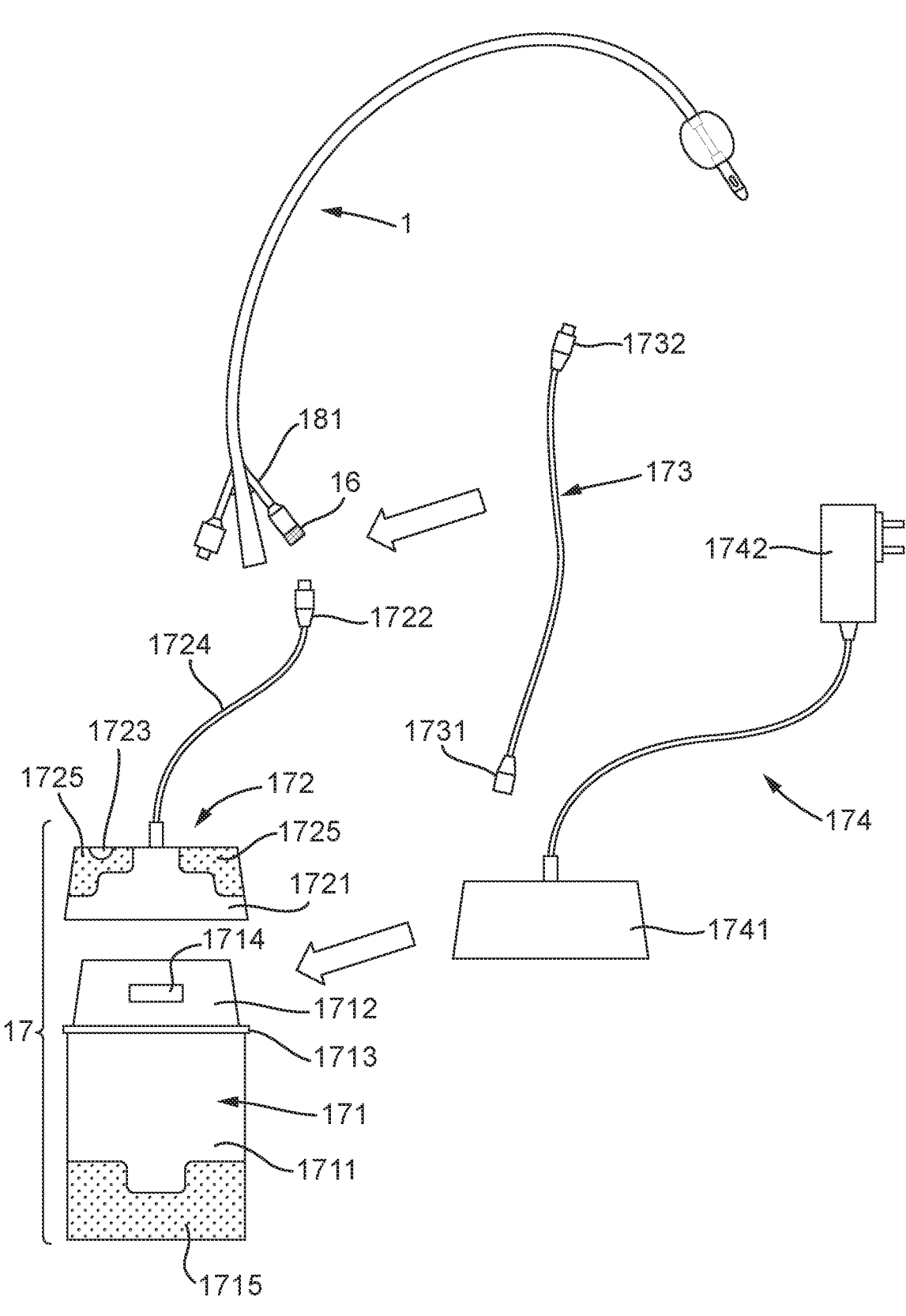
FIG. 8 shows an external power source for powering the at least one light generator in the catheter.

FIG. 8 shows a suitable external power source, such as a battery 17, for powering the at least one light generator 14, 15 in the catheter 1. As shown, the battery 17 may comprise a main body 171 and a connection module 172. The main body 171 may house battery cells 1711 providing a suitable voltage to the at least one light generator 14, 15. For example, the battery cells may provide at least a 3.1 V voltage, such as a 3.6 V voltage.

The battery cells 1711 may be lithium, lithium ion, lithium polymer, lithium air, solid state, aluminium ion or aluminium air cells. Cells may feature an lithium, sodium or potassium alkali-metal anode. Alternative energy sources may be used. For example, energy such as kinetic or thermal energy may be harvested from the user and converted to electric energy, such as through a thermoelectric generator (TEG) as described by Ren of the University of Colorado Boulder et al. (2021). Remote wireless power transfer may also reduce or eliminate the need for battery cells. Suitable technologies may include contactless magnetic induction, magnetic resonance and radio frequency waves (especially millimetre waves). Such technologies may employ lensing or beam forming technology and require the recipient device to transmit its location such as through a beacon antenna. Such a device, having the ability to wirelessly charge remotely, may include a receiving antenna array and a rectifier circuit to convert the wirelessly transmitted energy into electric energy. It should be understood that receivers able to receive energy remotely, without contact, can be placed anywhere on the device, such as directly on the at least one light generator. It should also be understood that transmitters able to wirelessly transmit energy may be supplied in a kit along with other elements of the device.

In a variation, the device may still contain battery cells, but utilise remote wireless recharging while remaining in situ on the user's person.

The connection module 172 may have an adapter portion 1721 and a counter-connector 1722. The main body 171 may have a mating portion 1712 configured to mate with the adapter portion 1721. Although not shown in the drawings, the adapter portion 1721 and the mating portion 1712 may have complementary metal contacts for connecting the battery cells to the adapter portion 1721 and, in turn, to the counter-connector 1722 via a power cord 1724. Any suitable metal contacts may be used. For example, spring-loaded metal pins, such as "pogo pins", may be provided in the adapter portion 1721 to electrically contact corresponding metal terminals provided on the mating portion 1712. The adapter portion 1721 and the complementary mating portion 1712 may each have an asymmetric arrangement, optionally asymmetric along both axes, so that they may fit together in a unique orientation. This may prevent inadvertent reversal of the polarity of the voltage supplied to the at least one light generator 14, 15.

Instead of metal contacts, magnetic induction may be used to transmit power between the main body 171 and the adapter portion 1721. This may provide a smooth surface on the main body 171 and the adapter portion 1721, so that dirt is less likely to accumulate. Similarly, the connectors and counter-connectors may transmit power by magnetic induction.

In view of the presence of fluids, the battery 17 may be provided within a waterproof housing. In particular, the main body 171 may be provided with a waterproofing member 1713. The waterproofing member 1713 may be configured to engage the adapter portion 1721 to form a waterproof seal. To maintain the waterproof seal, the mating portion 1712 may further comprise a protrusion 1714 configured to engage a corresponding recess (not shown) within the adapter portion 1721, so as to lock the adapter portion 1721 securely in place. The protrusion 1714 and the corresponding recess may also ensure that the main body 171 and the adapter portion 1721 are engageable in a unique orientation. When the main body 171 and the adapter portion 1721 are pushed together, an audible "click" may be produced, thereby providing an indication that the parts are properly connected. The connectors and counter-connectors may similarly be configured to produce an audible "click" when pushed together. The ports at the proximal end of the catheter such as the urine port and inflation port may similarly be configured to produce an audible "click" when pushed together in the correct orientation with a correct, corresponding part such as a urine bag, valve, or syringe, thereby providing an indication that the parts are properly connected. The main body 171 may be at least partially rubberised to facilitate detachment of the main body 171 from the adapter portion 1721. The rubberised part may comprise ridges to further enhance grip. Alternatively or additionally, the main body 171 and/or the adapter portion 1721 may have certain selectively texturised areas to enhance grip.

Some or all parts of the battery 17, including the main body 171, the housing of the mating portion 1712, the waterproofing member 1713 and the adapter portion 1721, may be made out of the same recyclable material, optionally polycarbonate.

One or more parts of the battery 17 may be manufactured through injection moulding at the same time, in the same mould as each other, such that (for instance) the main body 171 and the waterproofing member 1713 form a single component. Optionally, a mould tool may be used which selectively texturises part of the product (for instance the waterproofing member 1713).

Alternatively, the waterproofing member 1713 may be applied via either an over-moulding or a two-shot injection moulding process. Optionally, the waterproofing member 1713 may be made from a different material to the main body 171.

High grip regions 1715 of the main body 171 and high grip regions 1725 of the adapter portion 1721 may be designed so as to be easy to grip. High grip regions 1715 may be injection moulded from the same material as the main body 171 at the same time and using the same mould such that the main body 171 and the high grip regions 1715 are a single component made of the same material. Similarly, high grip regions 1725 and the adapter portion 1721, may be injection moulded at the same time, using the same mould such that the high grip regions 1725 and adapter portion 1721 are a single component made of the same material. Optionally, a mould tool may be used which provides a different finish texture between the high grip regions 1715 and the main body 171 and between the high grip regions 1725 and the adapter portion 1721, which may make it easier for the high grip regions 1715 and the high grip regions 1725 to be gripped.

Alternatively, high grip regions 1715 and high grip regions 1725 may be over moulded or produced through another method, potentially using another material. Optionally high grip regions 1715 and high grip regions 1725 may be part of a pouch or equivalent device which is applied to the main body 171 and the adapter portion 1721 and which may be removable by the user.

When viewed from above, the battery 17 may have an arc shape with both the main body 171 and the connection module 172 each having this arc shape. An arc shape may make it more obvious to the user in which orientation the main body 171 and the connection module 172 should be mated together. An arc shape may also improve the ergonomics of the battery 17 if it is placed against the user's leg.

To provide power to the catheter 1, the mating portion 1712 and the adapter portion 1721 may be fitted together, and the counter-connector 1722 may be connected to the power connector 16 of the catheter 1. The power cord 1724 may be of a length suitable for allowing the battery 17 to be placed within a pocket of the patient's clothing, such as about 20-100 cm, e.g. 22-50 cm or around 25 cm.

The adapter portion 1721 may comprise control circuitry (not shown) to control the supply of electrical power to the at least one light generator 14, 15. For example, the control circuitry may comprise resistors to limit the current supplied to the at least one light generator 14, 15. Alternatively, for greater energy efficiency, Buck converters may be provided to limit the current. The control circuitry may comprise a low-voltage detector configured to monitor the voltage output of the battery cells 1711. The low-voltage detector may be set to cut off voltage supply to the at least one light generator 14, 15 if the voltage falls below a predetermined threshold. The predetermined threshold may be 2-4 V, e.g. 2.5-3.5 V, or around 3.1 V.

The adapter portion 1721 may comprise an indicator light 1723. The indicator light 1723 may light up when the battery 17 is connected to the catheter 1. As noted above, the catheter 1 may comprise a third electric wire for detecting that a battery 17 is connected to the catheter 1. The control circuitry may use this detection as a trigger to provide power to the indicator light 1723. To conserve power, the indicator light 1723 may be flashed intermittently, such as every 1-4 seconds (e.g. every 2 seconds), and may remain on for a short period in the range 10-500 ms for each flash, e.g. for about 200 ms at a time. The indicator light 1723 may be an LED.

The adapter portion 1721 may alternatively comprise several indicator lights 1723. The indicator lights 1723 may be of different colours so as to convey different information. For instance, multiple green indicator lights may indicate correct functioning of a fully charged device with fewer illuminated indicator lights indicating a depleted charge. A red indicator light may indicate a fault with the device or that the battery cells 1711 are flat. A yellow indicator light may indicate that the battery cells 1711 are in need of charging. Another indicator light may indicate that the battery cells 1711 have degraded to the extent that the main body 171 with the battery cells 1711 needs to be disposed of or recycled. The battery 17 may determine that the battery cells 1711 have degraded by using a fuel gauge chip, recording information including the number of charging cycles or by starting a timer when they are first used.

As shown in FIG. 8, an extension cord 173 may be provided. The extension cord 173 may be used if the power cord 1724 is not long enough for a particular patient's clothing or preference. For example, the patient may prefer to place the battery 17 further away from the body. The extension cord 173 may be provided with an extension connector 1731 configured to mate with the counter-connector 1722 of the battery 17, and an extension counter-connector 1732 configured to mate with the power connector 16 of the catheter 1. It should be understood that several extension cords 173 may be connected together in series to further extend the power cord 1724 as necessary. When the extension cord 173 is connected to the power cord 1724 or the power connector 16, an audible "click" may be produced, thereby providing an indication that the parts are properly connected.

The battery cells 1711 may be rechargeable. A charging module 174 may be provided to recharge the battery cells 1711. The charging module 174 may comprise a power transformer 1742 and an adapter portion 1741. The adapter portion 1741 may be attached to the main body 171 in a similar way to the adapter portion 1721. The adapter portion 1741 may further be part of a dock (not shown). As part of the dock, the adapter portion 1741 may face generally upwards, so that the main body 171 may be dropped into the adapter portion 1741 vertically to create a connection. Successful coupling of the main body 171 to the adapter portion 1741 may be indicated by an audible "click" and or an indicator light. The power transformer may be plugged into a mains socket and output a voltage suitable for charging the battery cells 1711. For example, the power transformer may output 2-12 V DC, preferably around 4.5 V DC. The adapter portion 1741 of the charging module 173 may have substantially the same shape as the adapter portion 1721 of the connection module 172 and may be connected to the mating portion 1712 of the main body 171 of the battery 17. As with the adapter portion 1721 of the connection module 172, the adapter portion 1741 of the charging module 174 may have an asymmetrical arrangement so as to prevent inadvertent reversal of voltage polarity. Similarly, the connectors 16, 1731 and the counter-connectors 1722, 1732 may have an asymmetrical arrangement so as to prevent inadvertent reversal of voltage polarity. The bodies of the connectors 16, 1731 and the counter-connectors 1722, 1732 may have features indicating the correct orientation for mating, such as grooves, protrusions, markings or an asymmetrical structure. The counter connectors 1722, 1732 may be designed so as to only be able to mate with the connectors 16, 1731 in order to prevent inadvertent connection to an incompatible source.

Using a rechargeable battery, which is particularly easy to recharge by using the dock, may be more environmentally friendly than using a disposable battery. Furthermore, by limiting the regions irradiated and thus reducing power demand, this may enable the use of a rechargeable battery, which generally has a lower energy density than disposable batteries.

The material and colour of at least part of the battery 17 may be chosen so as to provide a surface which can be written on. Optionally the surface may be configured to allow for easy erasing of markings written on it. The surface may also be configured to allow for the easy attachment of stickers. In particular, the mating portion 1712 may be designed for noting information on. Such information may include the name of the patient to whom the device belongs, the date of first use of the device, or the time at which the battery cells were last recharged. Other information may be affixed or inscribed upon mating portion 1712, such as a serial number, barcode or QR code.

Battery 17 and/or catheter 1 may also feature Bluetooth, Wi-Fi, RFID, NFC, Ultra Wideband or other technology enabling communication between battery 17 and another device. Any of these technologies may facilitate recording details about the device in a health care worker's mobile smart device.

The battery 17 may comprise an alarm to indicate the state of the device. The alarm may indicate a battery cell in need of recharging or disposal, or a fault within the device. Such an alarm may be audible, generate a vibration and/or consist of a notification wirelessly transmitted to another device.

Although the catheter 1 of the present disclosure uses sterilising light for its sterilising action, it should be understood that this does not preclude the use of other modes of sterilisation. For example, the catheter 1 may comprise a lumen which may be pumped with air in order to compress and relax the elongate body 11 as a way to dislodge biofilms. Vibration may also be used to prevent adhesion of pathogens and biofilm, either by incorporating a vibration generator into the catheter 1 or by attaching an external vibration generator thereon. Such vibration generators may comprise an ultrasonic guided wave (UGW) transducer, as explored by Wang of Nanjing University et al. (2017). The catheter may also comprise materials or coatings having pathogen-inhibiting properties. For example, a polyethylene glycol (PEG), antibiotic or silver-alloy hydrogel coating may be used. Novel materials and surface textures may also be employed to prevent adhesion and mobility of pathogens. As with known catheters, antibiotics may be delivered up a lumen of the catheter while it is in situ.

What is claimed is:

1. A catheter for insertion into the bladder of a patient, the catheter comprising:

an elongate body having a distal portion configured to reside in the patient's body, and a proximal portion configured to be left outside of the body of the patient;

wherein the catheter further comprises a securing member that is configured to prevent the distal portion from exiting the patient's body;

wherein:

the catheter further comprises at least one light generator provided within the distal portion of the elongate body so as to emit light, wherein said light comprises sterilising light;

the elongate body defines a first internal lumen in fluid communication with the exterior of the elongate body though a fluid port, the fluid port being located in an end section of the distal portion, the end section being configured to reside within the bladder;

the elongate body defines a second internal lumen offset from the first internal lumen;

the at least one light generator comprises a distal light generator positioned in the second internal lumen to irradiate the fluid port;

the distal light generator and the fluid port are co-disposed at the same longitudinal position along the elongate body;

wherein the elongate body defines an opening on a side surface of the elongate body, and the opening provides access to the second internal lumen for positioning the distal light generator within the second internal lumen to irradiate the first fluid port; and wherein the opening is sealed after the distal light generator has been positioned in the second internal lumen to irradiate the fluid port.

2. The catheter of claim 1, wherein the light is blue or violet.

3. The catheter of claim 1, wherein the light comprises radiation within a spectral range of 390 to 500 nm.

4. The catheter of claim 3, wherein the total power of the radiation within the spectral range of 390 to 500 nm is at least 80% of the total power of the light.

5. The catheter of claim 3, wherein the light consists of radiation within a spectral range of 390 to 500 nm.

6. The catheter of claim 1, wherein the fluid port comprises two openings.

7. The catheter of claim 6, wherein the distal light generator is substantially equidistant from both openings of the fluid port.

8. The catheter of claim 1, wherein the at least one light generator comprises a proximal light generator positioned to irradiate and sterilise an area of a portion of the elongate body on the proximal side of the securing member.

9. The catheter of claim 8, wherein the proximal light generator is positioned such that the portion of the elongate body whose area is irradiated and sterilised by the proximal light generator is, when the distal portion is in the patient's body, located between the securing member and the internal urethral sphincter.

10. The catheter of claim 8, wherein the proximal light generator is positioned such that the portion of the elongate body whose area is irradiated and sterilised by the proximal light generator is, when the distal portion is in the patient's body including the bladder, located on the proximal side of the internal urethral sphincter.

11. The catheter of claim 8, wherein the proximal light generator comprises first and second light generating elements.

12. The catheter of claim 11, wherein the first light generating element faces the central axis of the elongate body, and the second light generating element faces an opposite direction to the first light generating element, away from the central axis of the elongate body.

13. The catheter of claim 12, wherein the first light generating element is configured to generate a greater power of sterilising light than the second light generating element.

14. The catheter of claim 1, further comprising a red-infrared light generator configured to emit at least one of red and infrared light and positioned to irradiate an area of a portion of the elongate body.

15. The catheter of claim 14, wherein the red-infrared light generator is configured to emit light selected from red light within a spectral range of 620 to 700 nm and infrared light within a spectral range of 800 to 2500 nm.

16. A method of producing a catheter, the method comprising the steps of:

providing a catheter comprising an elongate body having a distal portion and a proximal portion and a securing member configured to prevent the distal portion from exiting a body of a patient, wherein the elongate body defines first and second internal lumens in fluid communication with the exterior of the elongate body respectively through first and second fluid ports, the first and second fluid ports being located in said distal portion, the first fluid port being located in an end section of said distal portion, the end section being configured to reside within a bladder of the patient;

providing at least one light generator, wherein the at least one light generator comprises a distal light generator positioned to irradiate the first fluid port, and the distal light generator and the first fluid port are co-disposed at the same longitudinal position along the elongate body; and inserting the at least one light generator into the distal portion of the second internal lumen.

17. The method of claim 16, further comprising the step of sealing the second fluid port to close it.

18. The method of claim 17, wherein the step of sealing the second fluid port comprises injecting a sealant into the second fluid port to close the second fluid port, and optionally to fix the at least one light generator in place.

* * * * *